US006670115B1

(12) United States Patent
Zhang

(10) Patent No.: US 6,670,115 B1
(45) Date of Patent: Dec. 30, 2003

(54) DEVICES AND METHODS FOR DETECTING ANALYTES USING ELECTROSENSOR HAVING CAPTURE REAGENT

(75) Inventor: Honghua Zhang, San Diego, CA (US)

(73) Assignee: BioTronic Technologies, Inc., San Diego, CA (US)

( * ) Notice: Subject to any disclaimer, the term of this patent is extended or adjusted under 35 U.S.C. 154(b) by 0 days.

(21) Appl. No.: 09/699,140

(22) Filed: Oct. 27, 2000

Related U.S. Application Data

(60) Provisional application No. 60/167,409, filed on Nov. 24, 1999.

(51) Int. Cl.[7] .................. G01N 33/53; G01N 33/543; G01N 33/558
(52) U.S. Cl. .................. 435/5; 422/56; 422/57; 422/58; 422/61; 422/68.1; 204/193; 204/280; 204/400; 204/403; 204/412; 435/4; 435/7.1; 435/7.71; 435/7.72; 435/7.93; 435/7.94; 435/287.1; 435/970; 435/975; 436/501; 436/519; 436/518; 436/524; 436/538
(58) Field of Search .................. 422/56, 57, 58, 422/61, 68.1; 204/193, 400, 403, 412, 280; 435/4, 5, 7.1, 7.71, 7.72, 7.93, 7.94, 970, 975, 287.1; 436/501, 514, 518, 524, 538

(56) References Cited

U.S. PATENT DOCUMENTS

| | | | |
|---|---|---|---|
| 4,703,017 A | 10/1987 | Campbell et al. | 436/501 |
| 5,149,630 A | 9/1992 | Forrest et al. | 435/7.9 |
| 5,215,899 A | 6/1993 | Dattagupta | 435/6 |
| 5,271,895 A * | 12/1993 | McCroskey et al. | 422/101 |
| 5,286,362 A * | 2/1994 | Hoenes et al. | 435/7.1 |
| 5,391,272 A | 2/1995 | O'Daly et al. | 204/153.12 |
| 5,413,690 A * | 5/1995 | Kost et al. | 204/412 |
| 5,468,647 A | 11/1995 | Skold et al. | 436/514 |
| 5,580,794 A * | 12/1996 | Allen | 422/58 |
| 5,622,871 A | 4/1997 | May et al. | 436/514 |
| 5,658,444 A * | 8/1997 | Black et al. | 204/295 |
| 5,726,013 A * | 3/1998 | Clark | 422/55 |
| 5,753,517 A | 5/1998 | Brooks et al. | 436/514 |
| 5,756,362 A | 5/1998 | Durst et al. | 436/518 |
| 5,762,770 A * | 6/1998 | Pritchard et al. | 204/194 |
| 5,789,154 A * | 8/1998 | Durst et al. | 422/56 |
| 5,798,273 A | 8/1998 | Shiler et al. | 436/514 |
| 5,830,680 A | 11/1998 | Meyerhoff | 435/7.92 |
| 5,958,791 A * | 9/1999 | Roberts et al. | 204/403.14 |
| 5,972,199 A * | 10/1999 | Heller et al. | 204/403.1 |
| 6,100,045 A * | 8/2000 | Van Es | 204/403.14 |
| 6,174,734 B1 * | 1/2001 | Ito et al. | 435/7.1 |
| 6,305,214 B1 * | 10/2001 | Schattke et al. | 204/412 |
| 6,358,752 B1 * | 3/2002 | Durst et al. | 204/194 |
| 6,391,558 B1 | 5/2002 | Henkens et al. | 435/6 |
| 6,587,705 B1 * | 7/2003 | Kim et al. | 600/347 |

FOREIGN PATENT DOCUMENTS

| | | |
|---|---|---|
| EP | 0153875 A | 9/1985 |
| WO | WO 9852052 A | 11/1998 |

OTHER PUBLICATIONS

Zhang, H. et al. "A Fast and Rortable Electrochemical Immunosensor System", Abstract of Poster presented in the Pittcon'97 on Mar. 20, 1997 in Atlanta, Georgia.
Asakura, T. et al. (1978). *J Biol Chem* 253(28):6423–6425.
Boorsman, D.M. et al. (1976). *J Histochem Cytochem* 23:200–207.
Monroe, D. (1990). *Critical Reviews in Clinical Laboratory Sciences* 28(1):1–18.
Volpe, G. et al. (1998). *Analyst* 123:1303–1307.

* cited by examiner

*Primary Examiner*—Long V. Le
*Assistant Examiner*—Kartic Padmanabhan
(74) *Attorney, Agent, or Firm*—Morrison & Foerster LLP

(57) ABSTRACT

The present invention relates to devices comprising electrosensors containing capture reagents, their preparation thereof, and their use for detecting, preferably, quantitative measurement, of analyte in a liquid sample. In particular, the invention relates to an enzyme electrosensor, e.g., electroimmunosensor, device for electrochemical detection and preferably, real-time measurement, which is suitable for use at point-of-care settings by unskilled personnel.

36 Claims, 8 Drawing Sheets

Eight Analyte Array
(Ref/Aux in the Middle)

Four Analyte Array
(Ref/Aux in the Middle)

Nine Analyte Array
(With Dual Ref/Aux Sensing)

Four Analyte Lateral
( Ref/Aux in Periphery)

Six Analyte Lateral
( Ref/Aux in Periphery)

DEVICES AND METHODS FOR DETECTING ANALYTES USING ELECTROSENSOR HAVING CAPTURE REAGENT

The present application claims priority benefit of the provisional U.S. Patent Application Serial No. 60/167,409, filed Nov. 24, 1999, the content of which is herein incorporated by reference in its entirety.

FIELD OF THE INVENTION

The present invention relates to devices comprising electrosensors containing capture reagents, their preparation thereof, and their use for detecting, preferably, quantitative measurement, of analyte in a liquid sample. In particular, the invention relates to an enzyme electrosensor, e.g., electroimmunosensor, device for electrochemical detection and preferably, real-time measurement, which is suitable for use at point-of-care settings by unskilled personnel.

BACKGROUND OF THE INVENTION

There is an increasing public awareness of the need for diagnostics to determine levels of various components in human fluids, such as blood or serum. Of particular interest are tests designed for non-expert use that produce rapid and quantitative results.

Immunoassays have been widely used for the detection of antigens and antibodies. The most commonly used immunoassays are enzyme immunoassays (EIAs). The importance of EIAs, particularly in clinical analyses, medical diagnostics, pharmaceutical analyses, environmental control, food quality control, and bioprocess analyses, lies in their high sensitivity and specificity, which allow the detection of a wide spectrum of analytes in various sample matrices.

EIAs are commonly referred to as either heterogeneous (necessitating free antigen separation from those that have been bound to antibody) or homogeneous (requiring no separation or washing steps during the assay). Also, EIAs can be either competitive or non-competitive, depending on the availability of antibody binding sites. Conventional EIAs are convenient for analysis of great numbers of samples on a routine basis and are widely used in a broad spectrum of applications. However, these methods require multiple washing and incubation steps to implement, and can be utilized in high volume only by complex and expensive analytical equipment. The need for multiple washing and incubation steps has also limited the development of portable point-of-care analytical devices that can be used to perform assays in decentralized locations.

In recent years, efforts have been made to overcome the limitations of heterogeneous EIAs and to search for homogeneous, rapid, and separation-free immunoassays that can be readily conducted at the point of care. Fast and simple EIA tests capable of detecting a single analyte with a color change that can be visually interpreted have been developed. Based on the techniques of immobilizing antigen or antibody on a solid-phase support, assay formats such as dipsticks, test tubes, and wicking membrane test cartridges have been used to provide fast results for analytical conditions where a simple qualitative (yes/no) answer is clinically relevant. These membrane-based assays have gained increasing popularity in many areas of clinical chemistry. They not only form the basis of the majority of home use tests, but also are rapidly gaining use in the physician's office and hospital lab. These tests are widely accepted and increasingly used for detection of pregnancy, strep throat, and bacteria, as well as for prediction of ovulation. Examples of such assays are described in U.S. Pat. Nos. 5,622,871, 4,703,017, 5,468,647, 5,622,871, and 5,798,273. However, most of these rapid tests are incapable of performing sensitive and quantitative detection. As a result, medical diagnoses that require quantitative measurement of the target analyte remain within the domain of the complex immunoassay analyzers in the centralized laboratory.

A major trend in the development of rapid immunoassays is the move toward quantitative testing. The use of membrane-based immunoassays has been proposed for quantitative measurement of analytes. As a specific example, U.S. Pat. No. 5,753,517 describes a quantitative immunochromatographic assay utilizing antibody-coated particles, independent control particles, and capillary flow through a membrane. However, there are difficulties in developing such quantitative immunoassays based on membrane format for point-of-care diagnostic tests. Perhaps the most significant problems with the use of membrane-based immunoassays arise from requirements for the membrane that are contradictory. For example, immobilization of protein in the detection area requires that the membrane have a strong binding affinity for the protein, but transport of analyte and particles containing detection components demands that the membrane not bind to protein. Furthermore, factors commonly used for increasing the performance of the membrane assay are often mutually exclusive. For example, blocking reagents that reduce nonspecific interactions usually also reduce the amount of specific signal. In light of these competing requirements commonly seen in efforts to develop membrane-based immunoassays, it becomes clear that conventional membrane systems have limited advantages for use in quantitative immunoassays.

Accordingly, there is a need to develop improved assays, e.g., immunoassays, that can provide rapid, quantitative, and reliable results. The high sensitivity of electrochemical detection coupled with the inherent specificity of antibody-antigen reactions has resulted in a remarkable technique known as electrochemical immunoassay. The advantages of such assays include, among others, the ability to measure untreated samples in the presence of possible interfering substances, as well as the simplicity, and sensitivity associated with electrochemical detection.

Immunoassays employing amperometric electrochemical detection have been applied to the determination of analytes in fluid samples. An immunoassay device using amperometric detection to perform diagnostic tests for analytes in body fluids is described, as a specific example, in U.S. Pat. No. 5,830,680. The device includes an electrochemical detection system for a separation-free sandwich-type immunoassay, in which a protein analyte such as human chorionic gonadotropin (hCG) is sandwiched between a capture antibody immobilized on a microporous membrane gold electrode and an alkaline phosphatase-labeled antibody. Although such a device offers a separation-free feature, the time required for manipulating and incubating the sample limit the use of such assays for rapid diagnostic testing.

A method employing liposomes for signal production and electrochemical detection in immunoassays is described in U.S. Pat. No. 5,756,362. In these assays, liposomes that encapsulate an electroactive marker are conjugated with an analyte. A test device first allows incubation of a sample containing an analyte with a binding material specific for the analyte and the analyte-liposome conjugate. Following incubation, the mixture solution is allowed to traverse through an absorbent material strip to reach an electrochemical measurement portion where the liposome is lysed by a lysing reagent to release the electroactive marker. The amount of marker released is then detected electrochemically and correlated with the amount of analyte in the sample.

In the methods described in U.S. Pat. No. 5,391,272, bioactive components are coated onto colloidal gold and subsequently coated onto a sensor. Detection of analyte is achieved by measuring current generated by an electroactive species bound to the sensor as part of an analyte/enzyme catalytic response. Although the method is suitable for detecting several types of analytes (e.g. hormones or herbicides), it involves separation and incubation steps in order to achieve desirable sensitivity.

Other immunoassays using electrochemical detection have to rely on methods conventional in heterogeneous immunoassays, such as lengthy incubation time and multiple washing steps to separate free antigen and detection reagent from bound ones. Although several groups have reported methods for performing non-separation amperometric immunoassays, to date there have been no reports describing an amperometric immunoassay that is simple, rapid, and does not require a separation step.

Accordingly, there is still a need in the art for assay devices and methods that provide simple, quantitative and real time diagnostic measurements. The present invention addresses this other related needs in the art.

BRIEF DESCRIPTION OF THE INVENTION

The present invention overcomes many of the problems in the art by providing a simple, rapid, and reliable means to measure, and preferably, quantitatively measure, analyte in a liquid sample using a combination of electrochemical detection and binding between the analyte and its capture reagent.

In one aspect, the present invention is directed to a device for detecting an analyte in a liquid sample, which device comprises: a) a solid support; b) an electrosensor immobilized on said solid support, said electrosensor comprises a working electrode and another electrode used as auxiliary and/or reference electrode; c) a capture reagent immobilized on said working electrode, said capture reagent is capable of binding to an analyte; and d) conductive leads for connecting said electrodes to a readout device for electrochemical measurement.

The invention electrosensor, e.g., electroimmunosensor, utilizes a sensor assembly (i.e., sensor strip). The sensor strip can comprise a base sensor, e.g., a sensor fabricated by screen-printing of conductive materials onto a suitable support. A capture reagent that is capable of binding to the analyte is immobilized on the working electrode surface. Preferably, the capture reagent is capable of specific binding to the analyte, which can be either an antibody specific to an epitope of the analyte of interest, or the analyte of interest itself.

In addition to the sensor assembly, the device can optionally has a sample application area and/or a detection area. The detection area covers the region of the electrode surface upon which the capture reagent, e.g., antibody, is immobilized. The application area can include an application pad having a detection reagent pre-immobilized thereon. The detection reagent may be a detection reagent, e.g., an antibody, labeled with an enzyme that is able to produce an electrochemical detectable signal when reacting with substrates.

The sensor assembly can also include a wicking member, e.g., in the form of a strip, that connects the application area and the detection area. The wicking member functions as a carrier or wicking reagent to deliver the fluid sample containing the analyte and the detection reagent through capillary action to the detection area where they become immobilized on the electrode surface through, e.g., antibody-antigen reaction. Examples of materials useful as the wicking member include nylon, cellulose, paper, and the like. A preferred wicking member is a nylon mesh that has open mesh structure. A mesh structure is particularly useful because it has a two-dimensional structure suitable for lateral delivery of the liquid sample from the application area to the detection area to be in direct contact with the capturing reagent.

The sensor assembly may additionally include a conjugate releasing pad for absorption and controlled release of a conjugate and/or a separation filter for separating plasma from whole blood, resulting in the plasma wicking laterally.

An absorbent material used as waste reservoir can be positioned at the end of the sensor assembly, and overlaps with the wicking member to facilitate the migration of the sample through the device surface. The absorbent pad will have sufficient porosity and volume to retain a liquid sample on which the assay is to be performed.

In another aspect, the present invention is directed to a method for assaying an analyte in a liquid sample, which method comprises: a) contacting a liquid sample containing or suspected of containing an analyte with the above-described device under suitable conditions whereby the analyte, if there is any, binds to the capture reagent immobilized on the working electrode and the binding between the analyte and the capture reagent causes a change in the current signal that is capable of being detected by the electrosensor of the device; and b) detecting the change in the current signal generated in step a), whereby the presence or amount of the analyte in the sample is assessed.

In a preferred embodiment, the present method is used to perform an enzyme immunoassay using the invention electroimmunosensor. According to such a preferred method, a sample containing the analyte of interest is applied to the sample application area. The sample is allowed to flow through the membrane assembled in the sensor strip to react with the antibody immobilized on the sensor surface and with the antibody enzyme conjugate. Under appropriate conditions, the analyte is sandwiched between the antibody immobilized on the sensor surface and the antibody conjugate. The amount of analyte in the fluid sample is proportional to the amount of analyte immobilized on the sensor by this process through antibody-antigen interaction and can be detected through the antibody-enzyme conjugate that is bound to the sensor surface through the analyte. The amount of analyte is then determined from a standard curve for the analyte of interest.

Detection can be achieved according to the invention method by coupling the capture reagent-analyte binding reaction, e.g., immunological reaction, if the capture reagent used is antibody, to an electrode response using the enzyme conjugated to the analyte specific reagent as indicator. The current generated from a sensor assembly under controlled conditions is proportional to the analyte concentration present in the fluid sample and can be measured using a electrocurrent detection device, e.g., an amperometric monitor. Detection of analytes in buffer and serum samples can be accomplished using the invention electrosensors, e.g., electroimmunosensors, in either competitive or sandwich assay format.

Invention methods yield a rapid result by applying a test sample to a disposable sensor strip and initiating electrochemical detection when the invention electrosensor is connected to an electrochemical instrument, such as a hand-held detector. Good sensitivity and quantitative results can be achieved within minutes by unskilled personnel at point-of-care settings. Furthermore, the methods can generally be used for quantitative measurement of virtually any analytes, especially and immunologically active species, in a liquid sample, thus providing broad application in medical diagnostics and prognostics, and in agricultural and environmental assessments. In addition, the electrosensor can be provided in a kit suitable for use at home, in a physician's office, or in other point-of-care settings.

In still another aspect, the present invention is directed to a method for preparing an electrochemical sensor for the detection of an analyte in a liquid sample, which method comprises immobilizing a capture reagent capable of binding to an analyte on the surface of a hydrophobic, non-metal electrode by contacting said electrode surface with a solution containing said capture reagent and an organic immobilizing agent that wets said electrode surface and facilitates immobilization of said capture regent on said electrode surface.

In yet another aspect, the present invention is directed to a kit for detecting an analyte in a liquid sample, which kit comprises: a) a device comprising a solid support, an electrosensor immobilized on said solid support, said electrosensor comprises a working electrode and another electrode used as auxiliary and/or reference electrode, a capture reagent immobilized on said working electrode, said capture reagent is capable of binding to an analyte, and conductive leads for connecting said electrodes to a readout device for electrochemical measurement; and b) an effective amount of a suitable electron transfer mediator and substrate, and any other buffer solutions, conjugate solutions or, standards necessary for performing the detection assay.

In yet another aspect, the present invention is directed to a device for detecting an analyte in a liquid sample, which device comprises a sample application area that is in fluid communication with an electrosensor via a wicking member, wherein the wicking member has an open mesh structure.

DETAILED DESCRIPTION OF THE INVENTION

A. Definitions

Figure 1A:
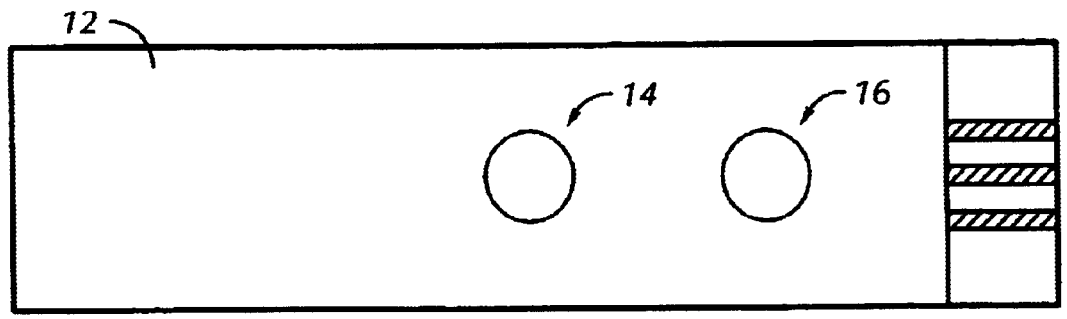
FIG. 1A is a schematic top view of an invention electroimmunosensor.

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "a capture reagent" refers to any agent that is capable of binding to an analyte. Preferably, "a capture reagent" refers to any agent that is capable of specifically binding to an analyte, i.e., having a higher binding affinity and/or specificity to the analyte than to any other moiety. Any moiety, such as a cell, a cellular organelle, an inorganic molecule, an organic molecule and a mixture or complex thereof can be used as a capture reagent so long that it has the desired binding affinity and/or specificity to the analyte. The capture reagent can be peptides, proteins, e.g., antibodies or receptors, oligonucleotides, nucleic acids, vitamins, oligosaccharides, carbohydrates, lipids, small molecules, or a complex thereof.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 daltons. More preferably, the small molecule has a molecular weight that is about or less than 5,000 dalton.

As used herein, "vitamin" refers to a trace organic substance required in certain biological species. Most vitamins function as components of certain coenzymes.

As used herein, "lipid" refers to water-insoluble, oily or greasy organic substances that are extractable from cells and tissues by nonpolar solvents, such as chloroform or ether.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants such as on viruses, cells, or other materials, drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, "antibody" includes antibody fragments, such as Fab fragments, which are composed of a light chain and the variable region of a heavy chain. Antibody encompasses polyclonal and monoclonal antibody.

As used herein, "labeled analyte" refers to labeled analyte, or any fragment, derivative or analogue thereof that substantially retains its binding affinity and/or specificity to the capture reagent so that the labeled analyte, or any fragment, derivative or analogue thereof, competes with unlabeled analyte in the sample fluid in binding to the immobilized capture reagent.

As used herein, "a label that is capable of generating electrocurrent under suitable conditions" refers to one or more, but not all component(s) that is required for generating current signal so that no electrocurrent can be generated in the absence of such label and current signal can only be generated, even in the presence of such a label, when other necessary current-generating component(s) is provided. For example, horseradish peroxidase, hydrogen peroxide and at least one electron transfer mediator(s), such as ferrocene, or a derivative thereof, benzoquinone, ascorbic acid or 3,3',5,5' tetramethylbenzidine, are needed to generate electrocurrent. Any one or two, but not all three, of the horseradish peroxidase, hydrogen peroxide and electron transfer mediator can be used as such a label(s).

As used herein, "in fluid communication" means that liquid can move from one part of the present device, e.g., a sample application area, to another part of the device, e.g., an electrosensor. The two or more parts of the device can be in fluid communication by being physically linked together or adjacent to each other, or the fluid communication can be mediated through another part of the device, e.g., a wicking member.

As used herein, "a detection reagent" refers to any agent that is necessary for generating a detectable current signal, which can be used to assess the presence and/or quantity of the analyte to be detected. The nature of a detection reagent is often determined by the assay format. For a competitive assay, a detection reagent can be a labeled analyte itself, or a fragment, analogue or derivative thereof that substantially retains its ability to bind to the analyte. In a competitive assay format, the capture reagent must be capable of specifically binding to an analyte. For a sandwich assay, a detection reagent can be a labeled reagent that is capable of binding to an analyte. In a sandwich assay format, at least one or both of the capture reagent and the detection reagent must be capable of specifically binding to an analyte.

As used herein, "a wicking member" refers to any substance or material or a mixture or complex thereof that enables fluid communication between different parts of the device by facilitating capillary flow of the fluid.

As used herein, "a wicking member having an open mesh structure" refers to woven or non-woven (extruded) fabrics made from filament fibers that enable uniform openings to be produced. Polyester, nylon, aramid, polyethylene, and glass fibers are among the many fibers available that are suitable for the applications.

As used herein the term "assessing" is intended to include quantitative and qualitative determination in the sense of obtaining an absolute value for the amount or concentration of the analyte, e.g., a protein or nucleic acid, present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further substance.

As used herein, "nutrient or storage protein" refers to a protein that is used by the cell as the nutrient source or storage form for such nutrient. Non-limiting examples of nutrient or storage proteins include gliadin, ovalbumin, casein, and ferritin.

As used herein, "contractile or motile protein" refers to a protein that endows cells and organisms with the ability to contract, to change shape, or to move about. Non-limiting examples of contractile or motile proteins include actin, myosin, tubulin and dynein.

As used herein, "structural protein" refers to a protein that serves as supporting filaments, cables, or sheets to give biological structures strength or protection. Non-limiting examples of structural proteins include keratin, fibroin, collagen, elastin and proteoglycans.

As used herein, "defense protein" refers to a protein that defends organisms against invasion by other species or protect them from injury. Non-limiting examples of defense proteins include antibodies, fibrinogen, thrombin, botulinus toxin, diphtheria toxin, snake venoms and ricin.

As used herein, "regulatory protein" refers to a protein that helps regulate cellular or physiological activity. Non-limiting examples of regulatory proteins include insulin, growth hormones, corticotropin and repressors.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target protein containing molecules prepared in vitro.

As used herein, "expressed in a tissue or organ specific manner" refers to a gene expression pattern in which a gene is expressed, either transiently or constitutively, only in certain tissues or organs, but not in other tissues or organs.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 $\mu$m) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "disease or disorder" refers to a pathological condition in an organism resulting from, e.g., infection or genetic defect, and characterized by identifiable symptoms.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

As used herein, "an immune system disease or disorder" refers to a pathological condition caused by a defect in the immune system. The immune system is a complex and highly developed system, yet its mission is simple: to seek and kill invaders. If a person is born with a severely defective immune system, death from infection by a virus, bacterium, fungus or parasite will occur. In severe combined immunodeficiency, lack of an enzyme means that toxic waste builds up inside immune system cells, killing them and thus devastating the immune system. A lack of immune system cells is also the basis for DiGeorge syndrome: improper development of the thymus gland means that T cell production is diminished. Most other immune disorders result from either an excessive immune response or an 'autoimmune attack'. For example, asthma, familial Mediterranean fever and Crohn disease (inflammatory bowel disease) all result from an over-reaction of the immune system, while autoimmune polyglandular syndrome and some facets of diabetes are due to the immune system attacking 'self' cells and molecules. A key part of the immune system's role is to differentiate between invaders and the body's own cells—when it fails to make this distinction, a reaction against 'self' cells and molecules causes autoimmune disease.

As used herein, "a metabolism disease or disorder" refers to a pathological condition caused by errors in metabolic processes. Metabolism is the means by which the body derives energy and synthesizes the other molecules it needs from the fats, carbohydrates and proteins we eat as food, by enzymatic reactions helped by minerals and vitamins. There is a significant level of tolerance of errors in the system: often, a mutation in one enzyme does not mean that the individual will suffer from a disease. A number of different enzymes may compete to modify the same molecule, and there may be more than one way to achieve the same end result for a variety of metabolic intermediates. Disease will only occur if a critical enzyme is disabled, or if a control mechanism for a metabolic pathway is affected.

As used herein, "a muscle and bone disease or disorder" refers to a pathological condition caused by defects in genes important for the formation and function of muscles, and connective tissues. Connective tissue is used herein as a broad term that includes bones, cartilage and tendons. For example, defects in fibrillin—a connective tissue protein that is important in making the tissue strong yet flexible—cause Marfan syndrome, while diastrophic dysplasia is caused by a defect in a sulfate transporter found in cartilage. Two diseases that originate through a defect in the muscle cells themselves are Duchenne muscular dystrophy (DMD) and myotonic dystrophy (DM). DM is another 'dynamic mutation' disease, similar to Huntington disease, that involves the expansion of a nucleotide repeat, this time in a muscle protein kinase gene. DMD involves a defect in the cytoskeletal protein, dystrophin, which is important for maintaining cell structure.

As used herein, "a nervous system disease or disorder" refers to a pathological condition caused by defects in the nervous system including the central nervous system, i.e., brain, and the peripheral nervous system. The brain and nervous system form an intricate network of electrical signals that are responsible for coordinating muscles, the senses, speech, memories, thought and emotion. Several diseases that directly affect the nervous system have a genetic component: some are due to a mutation in a single gene, others are proving to have a more complex mode of inheritance. As our understanding of the pathogenesis of neurodegenerative disorders deepens, common themes begin to emerge: Alzheimer brain plaques and the inclusion bodies found in Parkinson disease contain at least one common component, while Huntington disease, fragile X syndrome and spinocerebellar atrophy are all 'dynamic mutation' diseases in which there is an expansion of a DNA repeat sequence. Apoptosis is emerging as one of the molecular mechanisms invoked in several neurodegenerative diseases, as are other, specific, intracellular signaling events. The biosynthesis of myelin and the regulation of cholesterol traffic also figure in Charcot-Marie-Tooth and Neimann-Pick disease, respectively.

As used herein, "a signal disease or disorder" refers to a pathological condition caused by defects in the signal transudation process. Signal transudation within and between cells mean that they can communicate important information and act upon it. Hormones released from their site of synthesis carry a message to their target site, as in the case of leptin, which is released from adipose tissue (fat cells) and transported via the blood to the brain. Here, the leptin signals that enough has been eaten. Leptin binds to a receptor on the surface of hypothalamus cells, triggering subsequent intracellular signaling networks. Intracellular signaling defects account for several diseases, including cancers, ataxia telangiectasia and Cockayne syndrome. Faulty DNA repair mechanisms are also invoked in pathogenesis, since control of cell division, DNA synthesis and DNA repair all are inextricably linked. The end-result of many cell signals is to alter the expression of genes (transcription) by acting on DNA-binding proteins. Some diseases are the result of a lack of or a mutation in these proteins, which stop them from binding DNA in the normal way. Since signaling networks impinge on so many aspects of normal function, it is not surprising that so many diseases have at least some basis in a signaling defect.

As used herein, "a transporter disease or disorder" refers to a pathological condition caused by defects in a transporter, channel or pump. Transporters, channels or pumps that reside in cell membranes are key to maintaining the right balance of ions in cells, and are vital for transmitting signals from nerves to tissues. The consequences of defects in ion channels and transporters are diverse, depending on where they are located and what their cargo is. For example, in the heart, defects in potassium channels do not allow proper transmission of electrical impulses, resulting in the arrhythmia seen in long QT syndrome. In the lungs, failure of a sodium and chloride transporter found in epithelial cells leads to the congestion of cystic fibrosis, while one of the most common inherited forms of deafness, Pendred syndrome, looks to be associated with a defect in a sulphate transporter.

As used herein: stringency of hybridization in determining percentage mismatch is as follows: (1) high stringency: 0.1×SSPE, 0.1% SDS, 65° C.; (2) medium stringency: 0.2×SSPE, 0.1% SDS, 50° C.; and (3) low stringency: 1.0×SSPE, 0.1% SDS, 50° C. Equivalent stringencies may be achieved using alternative buffers, salts and temperatures.

For clarity of disclosure, and not by way of limitation, the detailed description of the invention is divided into the subsections that follow.

B. Devices and Kits

In one aspect, the present invention is directed to a device for detecting an analyte in a liquid sample, which device comprises: a) a solid support; b) an electrosensor immobilized on said solid support, said electrosensor comprises a working electrode and another electrode used as auxiliary and/or reference electrode; c) a capture reagent immobilized on said working electrode, said capture reagent is capable of binding to an analyte; and d) conductive leads for connecting said electrodes to a readout device for electrochemical measurement.

Any suitable solid support can be used in the present device. For example, plastic, polyvinyl chloride (PVC), polyvinylidene fluoride (PVDF), paper, nylon, fiberglass, polyethylene, nitrocellulose, a wicking member, e.g., a wicking member having an open mesh structure, or a combination thereof can be used as solid support in the present device.

The electrosensor of the present device must comprise a working electrode and another electrode used as auxiliary and/or reference electrode. In a specific embodiment, the electrosensor can comprise a working electrode, an auxiliary electrode and a reference electrode. In a preferred embodiment, , the working electrode and/or auxiliary electrode can comprise a screen-printed carbon conductor and the reference electrode can comprise a screen-printed silver or silver/silver chloride conductor.

Any capture reagent having desired binding affinity and/or specificity to the analyte can be used in the present device. For example, the capture reagent can be a cell, a cellular organelle, an inorganic molecule, an organic molecule and a mixture thereof.

Exemplary cells include animal, e.g., mammalian and human, plant, fungus e.g., yeast, and bacterium cells. Exemplary cellular organelles include nucleus, mitochondria, chloroplasts, ribosomes, ERs, Golgi apparatuses, lysosomes, proteasomes, secretory vesicles, vacuoles or microsomes, cytoplasm and other plasms within the such cellular organelles.

The capture reagent can be macromolecules such as peptides, proteins, e.g., antibodies or receptors, oligonucleotides, nucleic acids, e.g., nucleic acids capable of hybridizing with the target analyte nucleic acids under desired stringency, e.g., low, medium or high stringency, vitamins, oligosaccharides, carbohydrates, lipids, or small molecules, or a complex thereof.

Any proteins or peptides that are capable of binding, or specifically binding, to an analyte can be used as the capture reagent in the present device. For example, enzymes, transport proteins such as ion channels and pumps, nutrient or storage proteins, contractile or motile proteins such as actins and myosins, structural proteins, defense protein or regulatory proteins such as antibodies, hormones and growth factors can be used.

Any nucleic acids, including single-, double and triple-stranded nucleic acids, that are capable of binding, or specifically binding, to analyte can be used as the capture reagent in the present device. Examples of such nucleic acids include DNA, such as A-, B- or Z-form DNA, and RNA such as mRNA, tRNA and rRNA.

Any vitamins that are capable of binding, or specifically binding, to analyte can be used as the capture reagent in the present device. For example, water-soluble vitamins such as thiamine, riboflavin, nicotinic acid, pantothenic acid, pyridoxine, biotin, folate, vitamin $B_{12}$ and ascorbic acid can be used. Similarly, fat-soluble vitamins such as vitamin A, vitamin D, vitamin E, and vitamin K can be used.

Any lipids that are capable of binding, or specifically binding, to analyte can be used as the capture reagent in the present device. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

In a preferred embodiment, the capture reagent is an antibody, avidin/strepavidin, protein A or protein G.

The capture reagent can be immobilized on the working electrode by any methods know in the art. Preferably, the capture reagent is immobilized on the working electrode via a buffered organic solution containing a ketone or an aliphatic alcohol, e.g., isopropyl alcohol.

Any analyte, e.g., cells, cellular organelles, inorganic molecules, organic molecules and mixtures thereof can be detected by the present device. Preferably, the analyte to be detected is alpha-fetoprotein, prostate-specific antigen, cardiac troponins, c-reactive protein (CRP), or human chorionic gonadotropin, or a marker for HBV, HAV, HCV or HIV infection.

The device can further comprise an analyte bound to the capture reagent, said analyte contains a label that is capable of generating current signal under suitable conditions. When used, the analyte, if there is any in the sample fluid, will bind to the capture reagent immobilized and the binding between the unlabeled analyte in the sample and the capture reagent displaces the labeled analyte from the capture reagent and decreases current signal that is capable of being detected by the electrosensor of the device. The label can be an enzyme. Any enzyme that catalyzes a reaction that leads to the generation of current signal under suitable conditions can be used. In a specific embodiment, the enzyme is horseradish peroxidase and the enzymatic substrate is hydrogen peroxide and the electron transfer mediator is ferrocene, or a derivative thereof, benzoquinone, ascorbic acid or 3,3',5,5' tetramethylbenzidine.

The device can further comprise a cover casing having a liquid sample application aperture and a detection aperture.

The device can further comprise a sample application area that is separate, but in fluid communication with the electrosensor.

The device can be used in both the competitive and sandwich assay format. To be used in the competitive assay format, the sample application area can contain deposited labeled analyte, said labeled analyte is capable of being dissolved or suspended into the sample liquid and being carried to the capture reagent immobilized on the electrosensor by the sample fluid, and said label is capable of generating current under suitable conditions.

To be used in the sandwich assay format, the sample application area can contain deposited labeled detection reagent, said labeled detection reagent is capable of being dissolved or suspended into the sample liquid, binding to the analyte, if there is any, being carried to the capture reagent immobilized on the electrosensor by the sample fluid to form a sandwich comprising the immobilized capture reagent-analyte-labeled detection reagent, and said label is capable of generating electrocurrent current signal under suitable conditions. Preferably, the deposited labeled detection reagent is capable of specifically binding to the analyte, if there is any, in the sample fluid. Also preferably, the deposited labeled detection reagent is an antibody. The label can be an enzyme. Any enzyme that catalyzes a reaction that leads to the generation of electrocurrent under suitable conditions can be used. In a specific embodiment, the enzyme is horseradish peroxidase and the enzymatic substrate is hydrogen peroxide and the electron transfer mediator is ferrocene, or a derivative thereof, benzoquinone, ascorbic acid or 3, 3',5,5' tetramethylbenzidine.

The sample application area must be in fluid communication with the electrosensor. Preferably, the sample application area is in fluid communication with the electrosensor via a wicking member. Any suitable material or a mixture thereof can be used in the wicking member. Preferably, the wicking member comprises nylon, cellulose or paper. Also preferably, the wicking member comprises a nylon mesh having mesh opening in the range from about 0.45 $\mu$m to about 100 $\mu$m. Further preferably, the wicking member provides for substantially two dimensional transport of fluids from the application area to the electrosensor.

The device can further comprise a filter in the application area, said filter is capable of removing insoluble or insuspendable material(s) from the sample fluid. For example, the device can comprise a filter that is adapted for removing insoluble or insuspendable material(s) from a sample blood for the separation of plasma or serum from blood.

The device can further comprise an absorptive sink in fluid communication with the electrosensor, said sink having sufficient porosity and capacity to absorb excess liquid or allow excess liquid to be washed out of the device. The absorptive sink can use any suitable material and in any suitable geometric patterns. For example, the absorptive sink can be a pad of absorbent material.

In a specific embodiment, the device comprises an absorptive sink, an electrosensor and an application area that are linearly arranged in order.

The device can further comprise an enzyme substrate and an electron transfer mediator that are required for generating electrocurrent that can be detected by the electrosensor. Preferably, the enzyme substrate and the electron transfer mediator are localized on or in proximity to the electrosensor, said substrate and mediator can be controllably released.

In a specific embodiment, the present invention is directed to a device for detecting an analyte in a liquid sample, which device comprises: a) a base sensor strip having a working electrode, a reference electrode, and an auxiliary electrode coated on a plastic substrate, whereon a capture reagent is immobilized on the working electrode, said sensor strip having conductive leads for attaching the electrodes to a readout device for electrochemical measurement; b) a cover casing having a liquid sample application aperture and a detection aperture; c) an application zone for receiving a fluid containing an analyte from the application aperture, said application zone, in the dry unused form, containing a labeled detection reagent capable of specifically binding to said analyte, wherein the said labeled reagent is released into mobile form when in contact with the liquid sample; d) a detection zone in fluid communication with the electrodes in the presence of a liquid sample received from the detection aperture; e) a wicking member that carries the liquid sample from the application zone to the detection zone by capillary action, wherein said analyte is sandwiched between the detection reagent and the capture reagent immobilized on the electrode surface; and f) an absorbent sink placed in partial contact with the wicking member at the end of the flow path to absorb any excess fluid from the detection zone.

In another specific embodiment, the present invention is directed to a device for detecting an analyte in a liquid sample, which device comprises a sample application area that is in fluid communication with an electrosensor via a wicking member, wherein the wicking member has an open mesh structure. Preferably, the wicking member comprises a nylon mesh having mesh opening in the range from about 0.45 $\mu$m to about 100 $\mu$m. Also preferably, the wicking member provides for substantially two dimensional transport of fluids from the application area to the electrosensor. The device can further comprise a capture reagent capable of binding to an analyte that is immobilized on the electrosensor.

In still another specific embodiment, the present invention is directed to a kit for detecting an analyte in a liquid sample, which kit comprises: a) a device comprising: 1) a solid support; 2) an electrosensor immobilized on said solid support, said electrosensor comprises a working electrode and another electrode used as auxiliary and/or reference electrode; 3) a capture reagent immobilized on said working electrode, said capture reagent is capable of binding to an analyte; and 4) conductive leads for connecting said electrodes to a readout device for electrochemical measurement; and b) an effective amount of a suitable electron transfer mediator and substrate, and any other buffer solutions, conjugate solutions or, standards necessary for performing the detection assay.

C. Methods for Detecting Analytes

In another aspect, the present invention is directed to a method for assaying an analyte in a liquid sample, which method comprises: a) contacting a liquid sample containing or suspected of containing an analyte with a device comprising: 1) a solid support; 2) an electrosensor immobilized on said solid support, said electrosensor comprises a working electrode and another electrode used as auxiliary and/or reference electrode; 3) a capture reagent immobilized on said working electrode, said capture reagent is capable of binding to an analyte; and 4) conductive leads for connecting said electrodes to a readout device for electrochemical measurement, under suitable conditions whereby the analyte, if there is any, binds to the capture reagent immobilized on the working electrode and the binding between the analyte and the capture reagent causes a change in the electrocurrent that is capable of being detected by the electrosensor of the device; and b) detecting the change in the electrocurrent generated in step a), whereby the presence or amount of the analyte in the sample is assessed.

Any suitable capture reagent, including the capture reagents that are described in the above Section B can be used in the present method. Preferably, the capture reagent is an antibody. Also preferably, the capture reagent is capable of specifically binding to the analyte.

The present method can be used in both the competitive and sandwich assay formats. In a specific competitive assay format, the device used in the present method can comprise an analyte bound to the capture reagent, said analyte contains a label that is capable of generating current signal under suitable conditions, and the binding between the unlabeled analyte in the sample and the capture reagent displaces the labeled analyte from the capture reagent and decreases current signal that is capable of being detected by the electrosensor of the device. In an alternative competitive assay format, the device used in the present method can comprise a sample application area containing deposited labeled analyte, said labeled analyte is capable of being dissolved or suspended into the sample liquid and being carried to the capture reagent immobilized on the electrosensor by the sample fluid, said label is capable of generating electrocurrent under suitable conditions, and the presence of unlabeled analyte in the sample fluid decreases current signal that is capable of being detected by the electrosensor of the device. In still another alternative competitive assay format, the labeled analyte can be added in the sample fluid or can be added separately, said labeled analyte is capable of being dissolved or suspended into the sample liquid and being carried to the capture reagent immobilized on the electrosensor by the sample fluid, said label is capable of generating current signal under suitable conditions, and the presence of unlabeled analyte in the sample fluid decreases current signal that is capable of being detected by the electrosensor of the device.

In a specific sandwich assay format, the device used in the present method can further comprise a sample application area containing deposited labeled detection reagent, said labeled detection reagent is capable of being dissolved or suspended into the sample liquid, binding to the analyte, if there is any, being carried to the capture reagent immobilized on the electrosensor by the sample fluid to form a sandwich comprising the immobilized capture reagent-analyte-labeled detection reagent, and said label is capable of generating current signal under suitable conditions. Preferably, the deposited labeled detection reagent is capable of specifically binding to the analyte, e.g., an antibody, if there is any, in the sample fluid. In an alternative sandwich assay format, a labeled detection reagent can be added.in the sample fluid or can be added separately, said labeled detection reagent is capable of being dissolved or suspended into the sample liquid, binding to the analyte, if there is any, being carried to the capture reagent immobilized on the electrosensor by the sample fluid to form a sandwich comprising the immobilized capture reagent-analyte-labeled detection reagent, and said label is capable of generating current signal under suitable conditions. Preferably, the added labeled detection reagent is capable of specifically binding to the analyte, e.g., an antibody, if there is any, in the sample fluid.

The sample application area of the device used in the present method must be in fluid communication with the electrosensor. Preferably, the sample application area is in fluid communication with the electrosensor via a wicking member. Any suitable material or a mixture thereof can be used in the wicking member. Preferably, the wicking member comprises nylon, cellulose or paper. Also preferably, the wicking member comprises a nylon mesh having mesh opening in the range from about 0.45 µm to about 100 µm. Further preferably, the wicking member provides for substantially two dimensional transport of fluids from the application area to the electrosensor.

The device used in the present method can further comprise a filter in the application area, said filter is capable of removing insoluble or insuspendable material(s) from the sample fluid. For example, the device can comprise a filter that is adapted for removing insoluble or insuspendable material(s) from a sample blood.

The device used in the present method can further comprise an absorptive sink in fluid communication with the electrosensor, said sink having sufficient porosity and capacity to absorb excess liquid or allow excess liquid to be washed out of the device. The absorptive sink can use any suitable material and in any suitable geometric patterns. For example, the absorptive sink can be a pad of absorbent material.

In a specific embodiment, the device used in the present method comprises an absorptive sink, an electrosensor and an application area that are linearly arranged in order.

The device used in the present method can further comprise an enzyme substrate and an electron transfer mediator that are required for generating electrocurrent that can be detected by the electrosensor. Preferably, the enzymatic substrate and the electron transfer mediator are localized on or in proximity to the electrosensor, said substrate and mediator can be controllably released. Alternatively, the enzyme substrate and the electron transfer mediator are added in the sample fluid or is added separately for generating current signal that is capable of being detected by the electrosensor of the device.

The present method can be used to qualitatively or quantitatively detect any analyte. Preferably, the analyte to be detected is a marker for a biological pathway, a stage of cell cycle, a cell type, a tissue type, an organ type, a developmental stage, a disease, disorder or infection type or stage, or drug or other treatments. Exemplary tissues include connective, epithelium, muscle or nerve tissues. Exemplary organs include an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be manipulated. Exemplary internal animal organs include brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels. Exemplary diseases or disorders include neoplasm (neoplasia), cancers, immune system diseases or disorders, metabolism diseases or disorders, muscle and bone diseases or disorders, nervous system diseases or disorders, signal diseases or disorders, transporter diseases or disorders. Exemplary infections include the infections caused by viruses, bacteria or fungi. Preferably, the analyte to be detected is alpha-fetoprotein, prostate-specific antigen, cardiac troponins, c-reactive protein (CRP), or human chorionic gonadotropin or a marker for HBV, HAV, HCV or HIV infection.

Analyte from any fluid sample can be detected by the present method. Exemplary liquid sample include buffer, blood, serum, plasma, or urine, or a solution or suspension containing solid biological material.

In a specific embodiment, the present invention is directed to a method for assaying an analyte in a liquid sample, which method comprises: a) contacting a sample with a solution containing a labeled detection reagent that specifically binds to an analyte in the sample to form an assay mixture; b) incubating the assay mixture with a device comprising a solid support, an electrosensor immobilized on said solid support, said electrosensor comprises a working electrode and another electrode used as auxiliary and/or reference electrode, a capture reagent immobilized on said working electrode, said capture reagent is capable of binding to an analyte; and conductive leads for connecting said electrodes to a readout device for electrochemical measurement, for a time period sufficient for the analyte to become sandwiched between the labeled detection reagent and the capture reagent immobilized on the surface of the sensor; c) rinsing the electrosensor with an appropriate buffer solution; d) adding a detection solution containing a substrate and an electron transfer mediator to the sensor surface to initiate an electron transfer reaction; and e) determining current response generated from the electron transfer mediator catalyzed by the labeled detection reagent, whereby the presence or amount of analyte in the liquid sample is assessed.

In another specific embodiment, the present invention is directed to a method for assaying an analyte in a liquid sample, which method comprises: a) applying a fluid sample containing the analyte of interest to the application zone of the device comprising 1) a base sensor strip having a working electrode, a reference electrode, and an auxiliary electrode coated on a plastic substrate, whereon a capture reagent is immobilized on the working electrode, said sensor strip having conductive leads for attaching the electrodes to a readout device for electrochemical measurement; 2) a cover casing having a liquid sample application aperture and a detection aperture; 3) an application zone for receiving a fluid containing an analyte from the application aperture, said application zone, in the dry unused form, containing a labeled detection reagent capable of specifically binding to said analyte, wherein the said labeled reagent is released into mobile form when in contact with the liquid sample; 4) a detection zone in fluid communication with the electrodes in the presence of a liquid sample received from the detection aperture; 5) a wicking member that carries the liquid sample from the application zone to the detection zone by capillary action, wherein said analyte is sandwiched between the detection reagent and the capture reagent immobilized on the electrode surface; and 6) an absorbent sink placed in partial contact with the wicking member at the end of the flow path to absorb any excess fluid from the detection zone; b) allowing the liquid sample to transport from application zone to the detection zone by capillary action, wherein the analyte is sandwiched between the labeled reagent and the capture reagent immobilized on the sensor surface; c) adding a detection solution containing a substrate and an electron transfer mediator through the detection aperture to the detection zone to initiate an electron transfer reaction; and d)

amperometrically determining current response generated from the electron transfer mediator catalyzed by the labeled detection reagent, whereby the presence or amount of the analyte in the liquid sample is assessed.

D. Methods for Preparing Electrochemical Sensors Containing Capture Reagents

In still another aspect, the present invention is directed to a method for preparing an electrochemical sensor for the detection of an analyte in a liquid sample, which method comprises immobilizing a capture reagent capable of binding to an analyte on the surface of a hydrophobic, non-metal electrode by contacting said electrode surface with a solution containing said capture reagent and an organic immobilizing agent that wets said electrode surface and facilitates immobilization of said capture regent on said electrode surface.

Any suitable organic immobilizing agent can be used in the present method. Preferably, the organic immobilizing agent is a buffered aliphatic alcohol solution, e.g., isopropyl alcohol.

In a specific embodiment, the electrode is fabricated by screen printing carbon composition upon a plastic substrate.

In another specific embodiment, the electrode is a working electrode and is coupled with at least one additional electrode fabricated by screen printing a conductive composition upon a plastic substrate. Preferably, the working electrode and the additional electrode are fabricated by screen printing carbon composition upon the same plastic substrate.

Any suitable capture reagent, including the capture reagents described in the previous Sections B and C, can be used in the present method. For example, the capture reagent can be an amino acid, a peptide, a protein, a nucleoside, a nucleotide, an oligonucleotide, a nucleic acid, a vitamin, a monosaccharide, an oligosaccharide, a carbohydrate, a lipid or a complex thereof. Preferably, the capture reagent is. an antibody, avidin/strepavidin, protein A or protein G. Also preferably, the capture reagent is capable of specifically binding to an analyte.

The method can further comprise coating the electrode surface containing the immobilized capture reagent with a stabilizing solution that stabilizes the immobilized capture reagent. Preferably, the stabilizing solution stabilizes the capture reagent immobilized on the electrode in a dry form. Any suitable stabilizing solution can be used in the present method. Preferably, the stabilizing solution contains a sugar, a polyhydroxy compound, or STABILCOAT® (an aqueous solution containing purified bovine protein and other nontoxic chemicals in PBS buffer (phosphate buffered saline), pH 7.0–7.4).

E. Preferred Embodiments

In accordance with the present invention, there are provided electroimmunosensors and methods for rapid and quantitative measurement of the amount of various analytes in a variety of liquid matrices. The invention electroimmunosensor comprises a base sensor and a wicking member, which form a sensor assembly (i.e., sensor strip). See, for example, FIGS. 1 and 2.

Figure 1B:
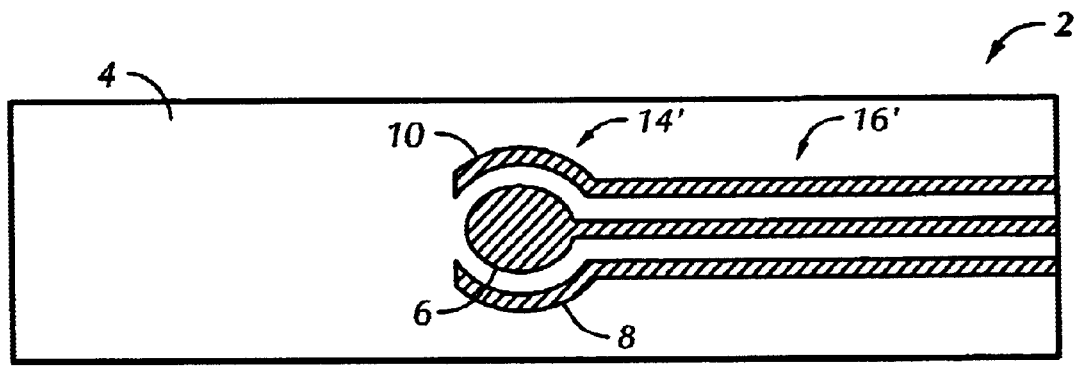
FIG. 1B is a schematic top view of a base sensor 2 used in an invention electroimmunosensor.

As shown in FIG. 1B, base sensor 2 comprises support 4 with working electrode 6, a reference electrode 8, and an auxiliary electrode 10 printed thereon. Base sensors may be prepared in a variety of ways, for example by screen-printing of a conducting ink, such as carbon ink, on a large sheet of suitable support, such as a sheet of MYLAR® (polyester) plastic, polyvinyl chloride (PVC), and the like. The support sheet can then be cut to produce individual sensors. The working electrode and the auxiliary electrode can both be printed using carbon ink. The reference electrode is preferably made using silver ink. To achieve better conductivity for the working and the counter electrode, a layer of silver ink can optionally be printed underneath the carbon ink. To provide an insulating layer, a layer of dielectric film can also be printed over of the conductive ink in the area of the printing that corresponds to sample application area. Sensors prepared in this manner can be used without further treatment for immobilization of a capture antibody thereon.

A capture reagent specific to the analyte, for example a primary antibody for a sandwich format immunoassay, is immobilized onto the working electrode surface by any suitable means, for example by spraying or spot casting. The capture reagent can be an antibody specific to an epitope of the analyte of interest, or can be the analyte of interest itself. The immobilized antibody is preferably a monoclonal antibody with specificity of $10^9$ liters/mole, or greater, for the analyte of interest.

FIG. 1A shows a covering that fits over and protects the base sensor 2. Cover 12 has two openings 14 and 16. When cover 12 is assembled with base sensor 2, openings 14 and 16 correspond to and expose underlying application area 14' and detection area 16', respectively, on the surface of the working electrode, which has the capture reagent immobilized thereon.

The three electrode leads shown in FIG. 1B form contacts for connection of the electroimmunosensor strip to a potentiostat for amperometric measurement of an electrochemically detectable species on the working electrode surface. In the presence of a liquid sample in the detection area 16', the electroimmunosensor functions as an electrochemical cell. Thus when a constant potential is applied to the working electrode with respect to the reference electrode, a current passes between the working electrode and the auxiliary electrode. The current flowing through the circuit is directly proportional to the amount of the detection reagent immobilized on the working electrode surface through the capture antibody, as is described in details below. Commercially available devices that can be used as potentiostat in accordance with the invention include BAS Electrochemical analyzer (West Lafayette, Ind.), Cypress System Electrochemical Analyzer (Lawrence, K S), AndCare Electrochemical Monitor (Durham, N.C.) and the like.

Alternatively, an electroimmunosensor with two electrodes (a working electrode and a reference electrode) can be used to replace the 3-electrode system in accordance with the invention methods when the solution resistance is negligible or the generated current is relatively small (for example, less than about 1 to about 5 $\mu$A). In this case, one electrode, for example printed in carbon ink, is used as the working electrode and the other electrode (for example printed in silver or silver chloride ink) functions as both reference electrode and auxiliary electrode. The working electrode is immobilized with a capture reagent. The 2-electrode sensor can be connected to an electrochemical device by conductive leads for electrochemical measurement.

The sensor assembly according to the invention (as illustrated, for example in FIG. 2) is designed for lateral flow of sample and reagents, moving from. left to right as shown in the Figure. The sensor assembly comprises a wicking member to provide for fluid flow from the application area 14 to the detection area 16. One important aspect of the present invention is the selection of a wicking member. The primary function of an invention wick for an electroimmunosensor is to act as a carrier for both the analyte in the sample and the conjugate so that both are allowed to flow through the wicking member and be captured on the electrode surface through an antibody immobilized on the electrode surface. Therefore, preferred attributes for a wicking member used in the invention electroimmunosensor include low protein binding, good flow characteristics, and water wetability. It is presently preferred that the wicking member have a consistent flow rate and, most importantly, that the flow is in a substantially lateral direction. A lateral flow profile is more advantageous than a flow profile containing both lateral and vertical directions. When a sample fluid flows through a membrane laterally in a thin layer, the analyte and conjugate are carried in closest proximity to the antibody immobilized on a sensor surface, resulting in an enhanced probability for formation of the antibody sandwich.

Membranes commonly used for other types of diagnostic tests, such as nitrocellulose membranes, usually have a microporous structure that generates flow in the vertical direction as well as lateral flow. However, the three dimensional microporous structure of membranes commonly used for other types of membrane-based-immunoassay are disadvantageous for a lateral-flow electroimmunosensor where the antibody is immobilized on the surface of the sensor. Because the capture antibody is immobilized on the surface-of the sensor, the mass transport of the analyte and the conjugate in the vertical direction generally limits the speed of the assay. Any diffusion of the analyte and conjugate in the vertical direction (as in microporous structures) does not contribute to the formation of a sandwich, but may contribute to a background signal caused by binding of the conjugate to the membrane.

Wicking members having an open mesh structure ensure a lateral flow profile while reducing the amount of non-specific signal and are, hence, considered particularly advantageous for use in the invention membrane-based electroimmunoassay. Another consideration for lateral-flow immunoassay tests is the rate of flow of fluids through the wicking material. Generally, a slow flow rate enhances the assay signal but increases the assay time as well. The wicking material having the most desirable set of attributes for use in the present invention is nylon mesh having a mesh opening sized in the range from about 10 $\mu$m to about 100 $\mu$m. A particularly suitable membrane material is nylon mesh made of Nylon PA 6,6, for example, as manufactured by Millipore (Bedford, Mass.) with open area up to 50% depending on mesh opening. These materials are inherently hydrophilic, thus ensuring instantaneous water wetting by capillary action without the use of surfactants or other additives.

The sensor assembly also includes an absorbent material (e.g., a pad) placed in partial contact with the wicking material at the end of the flow path (e.g., the outside edge of the detection area) to absorb and retain any excess fluid at the leading end of the lateral flow path. Thus, the absorbent pad can serve as a waste fluid reservoir. The absorbent material used in the absorbent pad can be any water absorbent, porous medium that is commercially available, such as Whatman absorbent paper, Grade WF1.5 and F427-07, which are currently preferred for use as the absorbent material in the absorbent pad.

The invention electroimmunosensor can further include a conjugate pad having a detection reagent, such as a secondary antibody labeled with an enzyme pre-immobilized thereon. The conjugate pad is placed in contact with the wicking material. When a sample is applied to the application area, the conjugate is re-hydrated and carried through the wicking material. Thus, the conjugate pad is particularly useful for conducting the electroimmunoassay in sandwich assay format. Examples of materials suitable for use as the conjugate releasing pad include borosilicate glass fibers with a maximum of 5% PVA.

The sensor assembly may also optionally include a separation filter through which fluids pass vertically (i.e., by wicking action). The separation filter can be used, for example, to separate plasma from whole blood.

Figure 2:
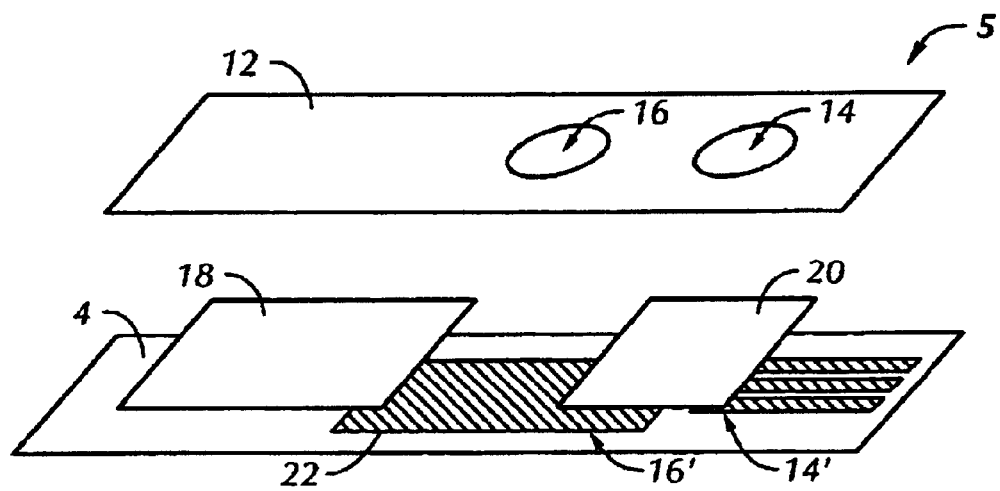
FIG. 2 is an exploded view of an invention electroimmunosensor.
Figure 3:
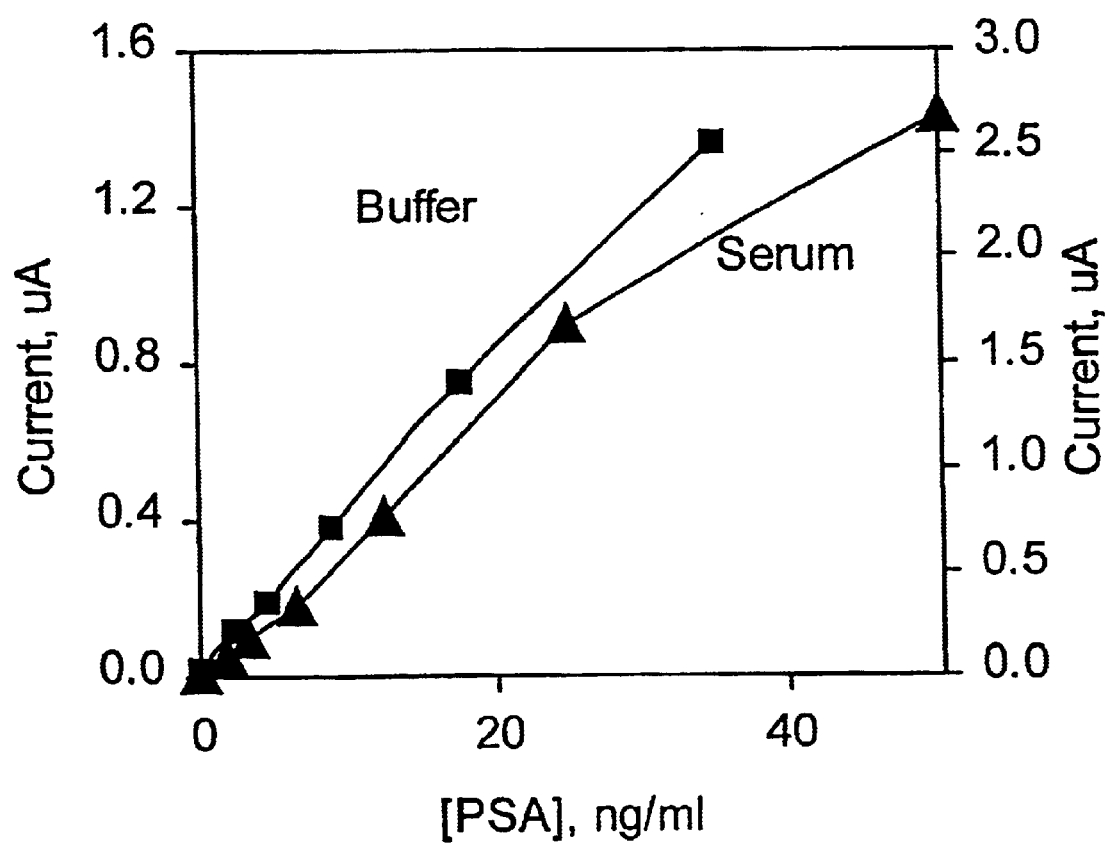
FIG. 3 is a graph showing the relationship of the amount of prostate specific antigen in buffer (-■-) and serum (-▲-) samples and the current response generated in the detection area of an invention electroimmunosensor.

The sensor assembly 5 (shown in exploded view in FIG. 2) is also designed for lateral flow of reagents (from left to right as shown in FIG. 2). In assembly 5 absorbent pad 18, wicking mesh 22 and conjugate pad 20 overlay the application area 14' and detection area 16', with absorbent pad 18 being in contact with the extreme leading edge of wicking strip 22 (shown to the left of the detection area 16') and with conjugate pad 20 being in contact with the opposite extreme edge of wicking strip 22. The detection reagent, for example, an antibody labeled with (e.g., conjugated with) an enzyme that is able to produce an electrochemical detectable signal when reacting with a substrate and electron transfer mediator, is immobilized on conjugate pad 20. Conjugate releasing pad 20 is for absorption and controlled release of a conjugate.

Wicking strip 22 connects the underlying application area 14' and the detection area 16' on the electrode surface and functions as a carrier to deliver the fluid sample containing the analyte and the detection reagent through capillary action to the detection area 16' where the analyte will become immobilized on the detection area of the electrode surface.

More specifically, when a sample containing an analyte is added to the sensor assembly 5 through opening 14, the sample first flows through the conjugate releasing pad 20 where contact with the sample causes release of the antibody-enzyme conjugate deposited or pre-immobilized on the conjugate releasing pad 20. The sample and the released antibody-conjugate reagent are then further carried through capillary action via wicking strip 22 past the detection area 16' on the sensor surface where the analyte is captured in a sandwich between the primary capture antibody immobilized thereon and the antibody conjugate containing the secondary antibody.

Electrochemical Enzyme Immunoassays (EEIA)

Combining the sensitivity of electrochemical detection with the selectivity and specificity of an immunoassay results in extremely sensitive assays having a lower detection limit and wider dynamic range than most other assay methods. Electrochemical detection is particularly advantageous for use in immunosensors in which the antigen-antibody reaction takes place on the surface of an electrode. Electrochemical detection is usually accomplished by amperometric detection of an electrode active species (electron transfer mediator) catalyzed by an enzyme in the presence of its substrate. See references: Ngo, T. T. Ed. *Electrochemical Sensors in Immunological Analysis,* Plenum Press. New York, 1987; and Monroe, D. "Amperometric Immunoassays" in *Critical Reviews in Clinical Laboratory Sciences.* 28 (1):1–18, 1990. Most commonly used enzyme labels for EEIA include alkaline phosphatase (AP) and horseradish peroxidase (HRP). In general, a desirable enzyme should be able to efficiently catalyze an electron transfer reaction of a suitable mediator in the presence of a substrate for the enzyme.

In one embodiment according to the present invention, a sandwich immunoassay format is used in which the enzyme horseradish peroxidase (HRP) is conjugated to the second antibody used to form the sandwich. Binding of an analyte specific to the immobilized antibody determines the quantity of enzyme-conjugated antibody at the electrode surface (and hence the amount of current generated by the electrochemical reaction involved in the assay), thus permitting the quantitation of the analyte of interest. Alternatively, a competitive immunoassay format can be used in which the enzyme horseradish peroxidase (HRP) is conjugated to the analyte. In this case the analyte and the analyte HRP conjugate compete for a limited number of binding sites on an antibody immobilized electrode surface. Due to the competitive nature of the assay, the amount of surface bound analyte-enzyme conjugate (and hence the amount of current generated by the electrochemical reaction involved in the assay) is inversely proportional to the concentration of the analyte in the sample.

The activity of the enzyme is determined electrochemically by the reduction of an electron transfer mediator. Examples of mediators that may be used in the assays of the invention include ferrocene and its derivatives, benzoquinone, ascorbic acid or 3,3',5,5' tetramethylbenzidine (TMB). TMB has been reported to be suitable for use in ELISA with spectrophotometric measurement and has been used as an electrochemical mediator for immunoassays where HRP is used as the enzyme (G. Volpe et al., *Analyst* 123:1303–1307, 1998). TMB is found to be a good substrate for amperometric determination of low levels of HRP and is preferred in the invention.

Thus, in the practice of invention methods the surface bound HRP conjugate is detected by adding preferred mediator TMB and hydrogen peroxide. The concentrations of both TMB and hydrogen peroxide are kept in excess in practice to ensure effective enzymatic reaction. In the presence of hydrogen peroxide as a co-substrate for HRP, TMB is oxidized and can then be reduced at a relatively low potential.

By using a low potential, for example, within the range from about 0 mV to about −200 mV (vs. Ag/AgCl), many biological processes that commonly interfere with electrochemical assays do not generate an interfering signal. The concentrations of the electron transfer mediator and substrate used are usually kept in excess of those required for the catalytic response of the enzyme. Under this condition, a steady-state current from the recycling of TMB on the electrode surface is generated for a given amount of HRP conjugate. Because the solid phase on which the sandwich is formed is also used for current measurement, for example by attachment of electrical leads thereto, a steady-state current can be reached within a few seconds after the addition of the substrate solution. The current generated is proportional to the amount of HRP conjugate bound to the electrode surface through the analyte. The substrate solution can be added to the detection area (FIG. 1) manually at the time of detection. Alternatively, the substrate solution may be sealed in a reservoir, such as an alumna pouch and prepackaged on the sensor or in fluid communication with the detection area. In the latter case, the solution can be released at the time of the assay by pressing the pouch or by controlled rupture of the pack by mechanical means.

To perform an enzyme immunoassay using the disposable invention electroimmunosensor, a sample containing the analyte of interest is applied to the sample application area. A detection reagent such as an enzyme antibody conjugate is released when in contact with the sample. The sample and the detection reagent are then allowed to flow through the wicking strip assembled in the sensor strip to form a complex with the antibody immobilized on the sensor. If a separation pad is present, for example for blood separation, the pad is positioned on top of a conjugate pad and facilitates separation of plasma from whole blood. Any excess of the fluid sample wicking through the strip will be drawn to the absorbent pad that serves as an absorbent sink. Under appropriate conditions, the analyte is sandwiched between the antibody immobilized on the sensor surface and the antibody conjugate. The amount of analyte immobilized from the fluid sample is proportional to the amount of analyte immobilized on the sensor through antibody-antigen interaction and can be detected through the antibody-enzyme conjugate that is bound to the sensor surface through the analyte.

Alternatively, an immunoassay can be performed using a base sensor where a capture antibody is immobilized on the working electrode. In this embodiment of the invention assay methods, a sample containing analyte of interest is mixed with an antibody enzyme conjugate. The mixture is applied to the sensor and incubated for a short time sufficient to allow formation of a complex between analyte and antibody enzyme conjugate in the sample and capture of the complex by the capture antibody, for example, for about 5 to about 30 minutes.

After the incubation, the sensor is rinsed with buffer solution to wash off unbound analyte and conjugate. The amount of immobilized analyte is then detected by addition of detection solution containing an enzyme substrate and an electron transfer mediator. A steady-state current generated in the electrode from the electrochemical reaction catalyzed by the enzyme is measured using a conventional current read-out device. The amount of current is proportional to the amount of analyte present in the sample solution.

In accordance with another embodiment of the present invention, test kits are provided for conducting a quantitative electroimmunoassay, for example using an invention electroimmunosensor. The invention kits comprise (a) a disposable sensor strip having at least one test area, in which a capture reagent is immobilized on the surface of the of the working electrode. The kit may further include other components, such as a hand-held monitor, standards for the analyte, buffer solutions and the like.

As used herein, the term "analyte" is defined broadly to include any species or moieties. The present invention is particularly applicable to virtually any analyte that generates antibody-antigen reaction. Representative examples of types of analytes include drugs, hormones, proteins, bacteria, viruses, and cancer markers, and the like. Illustrative examples of analytes that can be detected using the invention electroimmunosensors and methods include prostate specific antigen for prostate cancer detection; alpha-fetoprotein (AFP) and human chorionic gonadotropin (HCG) as markers for prenatal genetics screening, troponin I as acute myocardial infarction marker, and the like. The analyte may be determined in various liquid samples, including for example, serum, blood, urine, saliva, and the like.

Although antibodies are used herein as an example of an anti-analyte reagent since they are well characterized and understood, the anti-analyte reagent used in the invention methods and electroimmunosensor need not be limited to proteins and may be another type of macromolecule, whether naturally occurring, recombinant or synthetic, for example a synthetic receptor, a carbohydrate/protein complex or nonprotein moiety, to which a ligand or cross-reacting compound of interest will bind.

Nucleic Acid Detection

The device and the method can be adapted to a variety of target amplification techniques for the detection of amplified products. The commonly used amplification techniques include polymerase chain reaction (PCR) for DNA target amplification, and reverse transcriptase-PCR (RT-PCR), as well as isothermal nucleic acid amplification systems including nucleic acid sequence-based amplification (NASBA), the transcription-based amplification system (TAS), transcription mediated amplification (TMA), and the ligase chain reaction (LCR) system.

The detection of the amplified target can be achieved by hybridization of the target with a capture probe and a detector probe complementary to the target nucleic acid sequence, followed by electrochemical detection of the detector probe. To perform the assay, for example, a solution containing biotinylated detection probe and a fluoresceinated oligonucleotide probes can be added to the amplified reaction mixture. The capture probe and detection probe will specifically bind to target DNA or RNA molecules. The mixture solution can then be applied to a sensor containing a pre-coated Avidin-HRP or streptavidin-HRP conjugate as a detector reagent, and an anti-fluorescein antibody as a capture reagent. When the mixture solution flows through the sensor via capillary effect, the biotinylated portion of the probe will bind to the streptavidin conjugate pre-coated on a conjugate pad, while the fluoresceinated portion of the probe will be captured by the antifluorescein antibody immobilized on the working electrode. The HPR is detected electrochemically through a readout device. It should be kept in mind that while the basic format is generic for the detection of DNA/RNA target from an amplification technique, variations in assay design exist for different applications.

A particular advantage of the present invention is that quantitative assays can be performed by unskilled personnel requiring no more steps than adding sample solution or detection reagent. No lengthy incubation and sample separation are needed, and the whole assay can be performed within minutes.

The invention will now be described in greater detail by reference to the following non-limiting examples.

EXAMPLE 1

Preparation of Sensors by Printing

Base sensors as shown in FIG. 1 maybe purchased from a commercial source or fabricated by screen printing of conductive materials onto a suitable support, such as a plastic. The sensors used in the experiments were printed using a polyester screen and procedure recommended by the ink manufacture. The ink materials include silver conductor and carbon conductor (Polymer Thick film Compositions, 5000 and 7102, DuPont, Research Triangle Park, N.C.) and the support was MYLAR® (polyester) plastic. The working electrode and the auxiliary electrodes were both printed from carbon ink and the reference electrode was printed from silver ink on MYLAR® (polyester) plastic. To achieve better conductivity for the working and the counter electrode, a layer of silver ink was printed underneath the carbon ink. A layer of dielectric film can also be printed on top of the portion of the conductive leads to provide an insulating layer. Sensors prepared using such techniques can be used without further treatment for immobilization of a capture antibody.

EXAMPLE 2

Antibody Immobilization on Screen-printed Sensor

This example describes methods for immobilizing antibody on a screen-printed sensor surface using aliphatic alcohol solutions. It has long been know that certain organic solvents, including alcohols and ketones, have stabilizing effect on proteins at low concentrations, although these same organic solvents denature proteins at high concentrations (Adachi and Schwartz, *J Biol. Chem., 253*(28):6423–6425 (1978)). The presence of alcohols or ketones helps to wet the electrode surface and reduce static charge, thus facilitating the attachment of the protein to the surface.

Antibody was directly immobilized on carbon sensor surface by applying a buffered antibody solution (such as PBS) containing aliphatic alcohol. A preferred alcohol is iso-propanol. To immobilize an antibody on a screen-printed sensor, 3 $\mu$l of a capture antibody solution in 10 mM phosphate buffer containing iso-propanol was drop-coated on the working electrode area. The alcohol solution evaporates into the air at room temperature, leaving a layer of antibody bound to the electrode surface. The amount of antibody added to the sensor needs to be optimized for each capture antibody. Generally, however, the loading of sufficient antibody to provide about a monolayer of antibody coverage on the sensor surface gives the best sensor response. Antibody immobilized on the sensor surface by such a method generally retains its biological activity for at least a short period of time.

To further stabilize the antibody immobilized on sensor for long term usage, the antibody-coated surface was allowed to incubate in a solution containing 25% Stabil-Coat® (SurModics, Inc., Eden Prairie Minn.) and 0.01% Tween 20 at room temperature for 10 minutes. After the incubation, the solution was aspirated and the sensor was dried thoroughly before packaging in an airtight container with a desiccant.

The percentage of alcohol in the immobilization solution also influences the significance of the response. Experiments were conducted to compare the influence of the amount of iso-propanol used in an antibody immobilization solution. A monoclonal anti-alpha feto protein antibody in PBS buffer containing various percentage of isopropanol (in v/v %) was immobilized on the base sensor using the method described in the above section. The prepared sensors were incubated with a mixture solution containing 200 ng/ml alpha-fetoprotein (AFP) and an AFP-HRP conjugate at room temperature for 15 minutes. After the incubation the sensors were rinsed with PBS pH 7.4/0.5% Tween 20. The current response generated from the immobilized AFP-HRP on each sensor was measured using the method described in Example 3 herein. Table 1 below shows the result of the signal dependence on the percentage of iso-propanol used in the antibody immobilization solution. It has been found that a 25% isopropanol in PBS solution is generally suitable, and therefore is presently preferred for immobilization of most capture antibodies.

TABLE 1

| % isopropanol | Relative Response of Signal % Signal |
| --- | --- |
| 0 | 47.7 |
| 5 | 51.5 |
| 10 | 58.4 |
| 20 | 70.1 |
| 25 | 100 |
| 30 | 64.5 |

Methanol, ethanol, and ethyl acetate were also found to be suitable solvents for immobilizing antibody on the electrode. However results of immobilization tests indicated that the stability of sensors immobilized with antibody in ethanol solution decreases more dramatically over time than stability of antibodies immobilized in iso-propanol solution.

Techniques other than drop-coating can also be used for antibody immobilization. For example, the immobilization of antibody can be made by spraying an antibody solution on to the electrode surface, followed by evaporation of the solution. By spraying, the uniformity of antibody loading on the sensor can be controlled by selection of solvent and spray conditions. Furthermore, the spray casting technique is more suitable to mass production of the sensor for antibody immobilization.

EXAMPLE 3
Electrochemical Detection of HRP Conjugate

Binding of an analyte specific to immobilized antibody by a second antibody conjugated to an enzyme results in formation of a sandwich that permits quantitation of the analyte of interest through the enzyme conjugate. Activity of the enzyme can be determined electrochemically by reduction of an electroactive species (an electron transfer mediator) in the presence of a substrate for the enzyme. In the present example, the enzyme horseradish peroxidase (HRP) was conjugated to a second antibody. The electron transfer mediators that may be used for the invention include dimethylaminomethyl ferrocene, ascorbic acid, benzoquinone, and 3,3',5,5'-tetramethylbenzidine (TMB). A preferred mediator for amperometric determination of HRP activity is TMB. TMB has been reported to be suitable for use in ELISA with spectrophotometric measurement and has been used as an electrochemical mediator for immunoassays where HRP is used as the enzyme G. Volpe et al, supra. In tests of the sandwich assay format, TMB was found to be a good substrate for electrochemical detection of low levels of HRP. An optimized substrate comprised 40 $\mu$M TMB in 0.1M sodium acetate (pH 6.0) solution containing 5–10% dimethylsulfoxide, and 0.01% hydrogen peroxide as a co-substrate for HRP enzymatic reaction. Alternatively, ready-to-use liquid substrate solution containing TMB, buffer, and hydrogen peroxide can be obtained from commercial sources. Examples of such ready-to-use substrate solutions include ready-to-use K-BLUE® SUBSTRATE (TMB) (a stabilized mixture of 3,3',5,5'-tetramethylbenzidine (TMB) and hydrogen peroxide ($H_2O_2$) (Neogen Corporation, Lexington, Ky.) and 1-STEP™ TURBO TMB (a stabilized mixture of 3,3',5,5'-tetramethylbenzidine (TMB) and hydrogen peroxide ($H_2O_2$) (Pierce, Rockford, Ill.).

The enzyme activity of HRP immobilized on a sensor was measured using a Petite Ampere analyzer (Bioanalytical Systems, Inc., West Lafayette, Ind.). After the addition of the HRP substrate solution to a sensor connected to the monitor, a potential of –50 mV was applied. The current generated from HRP immobilized on the sensor was measured 5 seconds after the addition of the substrate solution.

EXAMPLE 4
Wicking Material (Membrane) Selection

The rate of capillary flow of buffer through several types of wicking materials was compared to determine the wicking properties of various materials. Porous membranes from various manufacturers were compared with nylon net filters having different size mesh openings (Millipore Corporation, Bedford, Mass.). Membranes were cut into 4 mm by 4.5 cm strips. Each membrane strip was fixed on a plastic support using a thin slice of transparent tape across one end of the membrane. A buffer solution (phosphate buffered saline (PBS)/0.5% casein, pH 7.4) was applied to each test membrane strip on the taped end. The time required for the fluid to flow through 4 cm of the test membrane was recorded. As shown in Table 2 below, the flow rate through porous membranes was generally slower than through membranes with mesh structure. Furthermore, within the range of mesh sizes tested, the flow of buffer through the membrane was directly proportional to the size of the openings in the mesh. While the actual speed of the test procedure will be determined by the flow rate of the membrane material employed, these tests showed that any of the membranes tested could be used to provide a rapid test. In addition, all the membranes tested showed consistent flow characteristics.

TABLE 2

| Membrane Type | Pore size | Time for buffer to flow 4 cm along membrane |
|---|---|---|
| Durapore, type SV | 5 $\mu$m | 3'26" |
| Durapore, type SV | 0.63 $\mu$m | 3'45" |
| Sartorius, cellulose Nitrate | 8 $\mu$m | 2'32" |
| Sartorius, cellulose acetate | 8 $\mu$m | 2'59" |
| Whatman, cellulose nitrate | 3 $\mu$m | 3'47" |
| Whatman, cellulose nitrate | 5 $\mu$m | 3'42" |
| NYLON NET FILTER | MESH OPENING | |
| Millipore, Nylon net | 11 $\mu$m | 1'33" |
| Millipore, nylon net | 30 $\mu$m | 1'05" |
| Millipore, nylon net | 80 $\mu$m | 49" |
| Millipore, nylon net | 100 $\mu$m | 40" |

The performance of the test wicking materials (membranes) in electroimmunosensor response was compared using each of the membranes in an invention electroimmunosensor. Anti-alpha-fetoprotein (AFP) antibody was immobilized on a sensor using the procedure as described in the Example 2 above. As second antibody for the sandwich assay, an anti-AFP-HRP conjugate was deposited and dried on a conjugate pad. The conjugate pads and sensor strips utilizing the various test membranes were prepared using procedures described in Example 7 hereinbelow. All the wicking materials used in this example were unblocked.

To each sensor strip was added 100 $\mu$l of 200 ng/ml AFP in PBS/0.5% Casein, pH 7.4 solution. The sample was allowed to flow through the test membrane assembled in the sensor strip to react with the antibody immobilized on the sensor surface and with the antibody-HRP conjugate. Electrochemical signal was measured using a TMB/$H_2O_2$ substrate solution. The background response from nonspecific signal was compared with the response from the analyte by adding buffer solution without analyte to a sensor strip. Table 3 below shows the results of these tests:

TABLE 3

| Membrane Type | Pore size | Signal $\mu$A | Background $\mu$A |
|---|---|---|---|
| Durapore, type SV | 0.63 $\mu$m | 4.01 | 2.51 |
| Sartorius, cellulose Nitrate | 8 $\mu$m | 2.00 | 1.12 |
| Sartorius, cellulose acetate | 8 $\mu$m | 1.83 | 0.99 |
| Whatman, cellulose nitrate | 3 $\mu$m | 4.36 | 2.44 |
| Whatman, cellulose nitrate | 5 $\mu$m | 0.97 | 0.55 |
| Millipore, nylon net | 30 $\mu$m | 3.03 | 0.47 |

These results indicate that membranes with porous structure generally generate much higher background signal than wicking materials with mesh structure. On the other hand, even though the flow of the test solutions in wicking materials with mesh structure was much faster than in membranes with porous structure (see Table 2), a significant signal was generated, indicative of more efficient antibody-antigen binding conditions. These data demonstrate that wicking materials with mesh structure resulted in the lowest background signal and highest signal-to-noise (S/N) ratio compared with porous membranes, proving that wicking materials with mesh structure are presently preferred for use in the invention electroimmunosensors and methods.

Although wicking materials with mesh structure, such as nylon net, are a preferred material for use as the membrane in the invention electroimmunosensor, it is to be understood that other materials having similar structure or having porous structure may also be used for producing similar effect when they are optimized to reduce the nonspecific signal.

EXAMPLE 5

Selection of Membrane Blocking Agents to Reduce Nonspecific Signal

The electroimmunosensor response can be further improved by blocking the wicking strip used in a sensor strip. The membrane strip is blocked for the following purposes, among others: 1) to reduce non-specific binding of the antibody-conjugate or analyte to the membrane surface, and 2) to improve re-wetting and storage properties of the finished device. Nonspecific attachment to the wicking material can normally be reduced by blocking with a protein (e.g. casein or bovine serum albumin), surfactant (e.g., Tween 20, or Triton X-100), or a polymer (e.g., polyvinyl alcohol).

A preferred blocking agent in the invention is a polymer having a hydrophobic center block and hydrophilic end blocks with the structure PEG-PPG-PEG (where "PEG" is poly(ethylene glycol) and "PPO" is poly(propylene glycol). Examples of such polymers are such as PLURONIC™ (block copolymers of ethylene oxide (EO) and propylene oxide (PO)) (BASF Corporation, North Mount Olive, N.J.) and POLOXAMER™ (a tri-block copolymer of poly ethylene oxide and polypropylene oxide). The center blocks can adsorb onto a hydrophobic surface with the end blocks extending from the surface and waving freely like seaweed. The coverage of the hydrophobic center and the action of the hydrophilic end blocks effectively block the membrane surface and create a surface that does not absorb proteins.

To examine the effect of blocking reagent on nonspecific signal, experiments were conducted under conditions similar to those under which electroimmunosensor assays are performed to determine the amount of HRP-antibody conjugate retained on a blocked wicking material. The selected blocking reagents include (a) a PEG-PPG-PEG polymer (average $M_n$ 8,400), (b) Triton X-100, (c) PVA ($M_w$ 13,00–23000), and (d) (Tween 20), all from Aldrich Chemical Company, Inc., Milwaukee, Wis. Dry wicking strips (nylon mesh, 30 $\mu$m mesh opening, Millipore) were soaked in solutions containing 1% of a blocking reagent, and allowed to equilibrate overnight at 4° C. without shaking. The wicking strips were then dried at room temperature and cut into sections (0.5 cm by 2 cm) and assembled on a base sensor immobilized with a capture antibody against troponin I, together with a absorbent pad and a conjugate pad containing 30 ng/pad of a pre-dried anti-troponin I HRP conjugate. 150 $\mu$L of PBS pH 7.4/0.5% casein buffer was applied to the application area of each electroimmunosensor and allowed to flow through. After 5 minutes, three drops of a substrate solution containing TMB/H2O2 were applied to the detection area. The current signal from each sensor strip was measured electrochemically using the method described in Example 3.

The result indicates that comparing to wicking strip without blocking, all the blocking reagents showed some effect in reducing the nonspecific signal due to the attachment of the HRP conjugate to the wicking strip. The effectiveness of blocking is in the order: PEG-PPG-PEG>>PVA>Triton X-100>Tween 20. The amount of blocking reagent used in the blocking solution is also found influencing the amount of nonspecific signal. In general, the nonspecific signal decreases with the increase of the amount of blocking reagent used in blocking the wicking strip.

EXAMPLE 6

Antibody-HRP Conjugation

Many antibody-HRP conjugates are commercially available. Alternatively, an antibody-HRP-conjugate can be made using Pierce's EZ-LINK™ Plus Activated Peroxidase kit (peroxidase containing amine-reactive HRP derivative) (Pierce Chemical, Rockford, Ill.) and a procedure described as follows:

1. Dissolve approximately 1 mg IgG into 0.5–1.0 ml phosphate buffered saline.
2. Reconstitute 1 mg of lyophilized EZ-LINK™ Plus Activated Peroxidase (peroxidase containing amine-reactive HRP derivative) with 100 $\mu$l of water and add to the IgG solution.
3. Immediately add 10 $\mu$l of sodium cyanoborohydride solution, composed of 5 M NaCNBH$_3$ in 1 M NaOH.
4. Incubate the solution at room temperature for one hour.
5. Add 20 $\mu$l of quench buffer composed of 3M ethanolamine, pH 9.0 and react at room temperature for an additional 15 minutes.
6. Dialyze the conjugate in PBS solution using a Dispo-Dialyzer from Spectrum with 100,000 molecular weight cut off (MWCO) to remove free HRP from the conjugate solution.
7. Add Piece's SUPERFREEZE™ (a solution containing ethylene glycol and preservatives) Peroxidase Conjugate Stabilizer to the conjugate solution and store the solution in the refrigerator for long term storage.

EXAMPLE 7

Conditions for Conjugate Releasing

A variety of materials can be used as the conjugate releasing pad in the invention electroimmunosensor assays, for example, borosilicate glass fiber with polyvinyl acrylic binder or materials with polyester matrixes. The attributes to be sought in selection of the material for fabrication of the conjugate releasing pad include low protein binding, consistent flow characteristics, uniform release of the conjugate and the like. A preferred conjugate releasing material is LOPROSORB® (glass fiber membrane) (KK0141 Gelman Sciences, Ann Arbor, Mich.).

In assays described herein, the conjugate releasing pad is prepared by drying antibody conjugates onto the releasing pad. The conjugate can be applied to the conjugate releasing pad either by spraying a solution of the conjugate from a spray bottle or by manual addition of the conjugate solution to the conjugate releasing material with a micropipette. In the present example, an antibody-HRP conjugate solution is diluted in 20% buffered sucrose solution for application to the conjugate releasing pad. The conjugate pad is dried before being placed in contact with the lateral flow membrane in the sample application area. When a liquid sample is applied to the application area, the conjugate is rehydrated and carried through the membrane.

EXAMPLE 8
Disposable Sensor Strip for Prostate-Specific Antigen Detection

Figure 4:
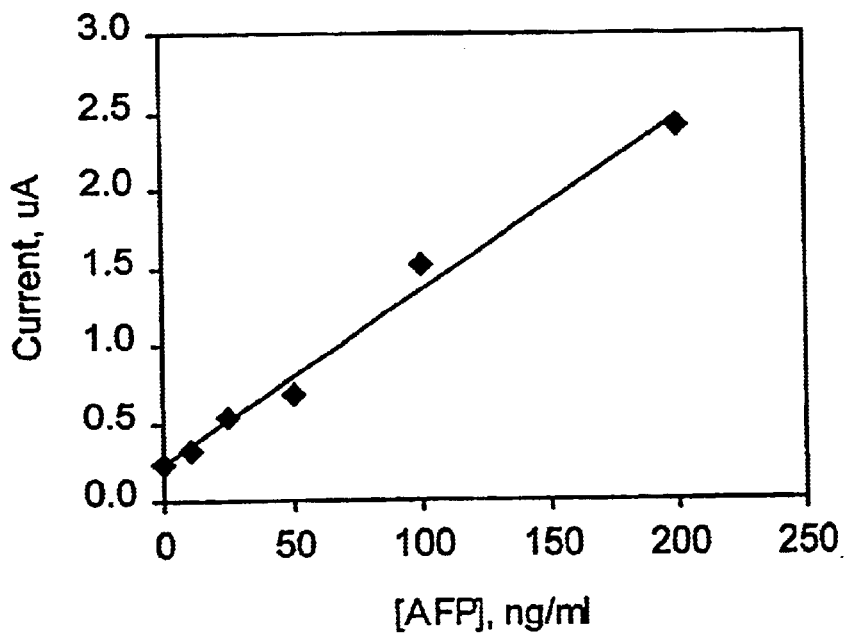
FIG. 4 is a graph showing the relationship between the amount of alpha amino-fetoprotein (AFP) in a fluid sample and the current response in the detection area using sensor strip format.

Base sensors of the type shown in FIG. 2 can be used alone for the detection of analytes in a variety of liquids by applying a sample containing the analyte of interest directly to the detection area where an antibody is immobilized. In the present example, such a base sensor was used for the detection of prostate specific antigen (PSA) by immobilizing a monoclonal anti-PSA antibody on the sensor strip using methods described in Example 2 above. PSA in a PBS pH 7.4/0.5% casein solution and serum sample were incubated concurrently with a second monoclonal anti-PSA antibody-HRP conjugate, resulting in the capture of the conjugate on the surface of the base sensor. After a 10-minute incubation at room temperature, the sensor strip was rinsed with a PBS/0.05% Tween 20, pH 7.4 solution, followed by addition of a substrate solution containing hydrogen peroxide and TMB. The electrical leads from the sensor were attached to a read-out device (Petite Ampere, Bioanalytical Systems Inc., West Lafayette, Ind.), and the resultant current was measured 5 seconds after addition of the substrate solution. As is shown in FIG. 4, the current response was directly proportional to the amount of PSA present in the test sample. Examples of analytes that can be detected in this way include, but are not limited to, human chorionic gonadotropin (hCG), c-reactive protein and alpha-fetoprotein (AFP).

EXAMPLE 9
Sandwich Assay Using Disposable Sensor Assembly

A sandwich-type electroimmunosensor assay may also be performed for the detection of alpha-fetoprotein (AFP) using a disposable membrane sensor in accordance with the present invention. In this example, 3 µl of 15 µg/ml anti-AFP-HRP conjugate purified according to the method described by Boorsman, D. M. et. al. (*J. Histochem. Cytochem.* 23:200–207, 1976) was deposited on a low protein binding conjugate pad from Gelman Sciences (LOPROSORB® (glass fiber membrane), KK0141). The conjugate pad was allowed to dry at room temperature for 20 minutes and stored in a humidity controlled chamber overnight before assembly into a sensor strip. Then 30 ng/sensor of a monoclonal anti-AFP was immobilized on the sensors and the sensor was assembled as described above.

Figure 5:
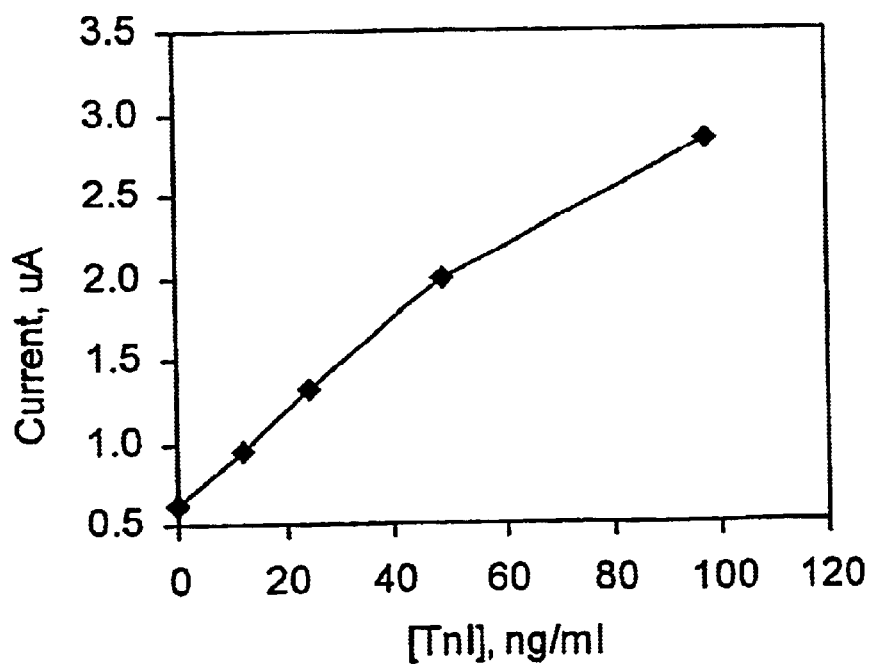
FIG. 5 shows the electrochemical response of cardiac troponin I in a fluid sample measured with an invention electroimmunosensor.

To perform an enzyme immunoassay using the disposable electroimmunosensor, 200 µl of a sample solution containing AFP in PBS/0.5% casein, pH 7.4 was applied to the sample application area. The sample was allowed to flow through the wicking membrane in the sensor strip to react with the antibody immobilized on the sensor surface and with the antibody enzyme conjugate. After a few minutes, a 100 µl/sensor of substrate solution containing TMB/$H_2O_2$ was added to the detection area of the sensor. The current was measured 5 seconds after the addition of the substrate solution using a, read-out device (Petite Ampere, Bioanalytical Systems, Lafayette, Ind.) connected to the sensor strip. As is demonstrated in FIG. 5, the signal detected in the detection area was continuously increased as the concentration of the analyte in the fluid sample is increased.

In a similar way, the electroimmunosensor can be used to detect a cardiac marker troponin I (TnI) for the detection of cardiac injury. The electroimmunosensor for the assay prepared using the described methods is assembled with a base sensor, an absorbent pad, a conjugate pad, and a nylon mesh (30 µm Millipore). In each sensor is immobilized about 45 ng of a monoclonal on the surface of the working electrode; the conjugate pad contains 30 ng of second antibody against Troponin I that is conjugated to HRP. The membrane used in this example are pre-blocked with 2% PEG-PPG-PEG (Mn 8400). To perform the assay, 150 µl of a sample liquid containing TnI is applied to the sensor in the application area. After 5 minutes, ready-to-use K-BLUE® SUBSTRATE (TMB) (a stabilized mixture of 3,3',5,5'-tetramethylbenzidine (TMB) and hydrogen peroxide ($H_2O_2$) TMB (Neogen Corporation, Lexington, Ky.) was added to the detection area. The current was measured 5 seconds after the addition of the substrate solution using a read-out device (Petite Ampere, Bioanalytical Systems, Lafayette, Ind.) connected to the sensor strip. The result, shown in FIG. 5, demonstrated that the, amount of troponin I present in the liquid sample solution can be measured quantitatively over the clinical relevant range using the invention electroimmunosensor.

EXAMPLE 10
Development of a New Immunosensor for Clinical Diagnosis: A Disposable System with Lateral-flow Design and Amperometric Detection Introduction The development of a rapid, sensitive, and separation-free method for the analyses of various analytes has been a long-standing goal for biosensor technology. We have developed a novel immunosensor system that combines the advantages of the specificity of immunoassay, the fast reaction time of lateral-flow chromatographic membrane assay, and the sensitivity of electrochemical detection.

The system is based on the principle of immunoassay coupled with amperometric detection using an enzyme as an indicator. The sensor system comprises screen-printed electrodes immobilized with antibodies. A nylon mesh is used as wicking agent for sample delivery via capillary action, and an absorbent sink is placed at the end of the flow path to absorb excess sample fluid. Lengthy incubation and separation steps are eliminated by the lateral flow sensor design with membrane materials and dry reagents incorporated on the sensor. The sensor system has high sensitivity and specificity, and is packaged into convenient and miniaturized device that can be used at the point-of-care settings.

Design of the System

The design of the immunosensor system includes the development for (1) a monitor for amperometric signal detection, (2) an antibody immobilized base sensor, and (3) a sensor assembly containing base sensor, all the reagents in dry form, and means for sample handling as well as reagent delivery.

Monitor

Figure 6:
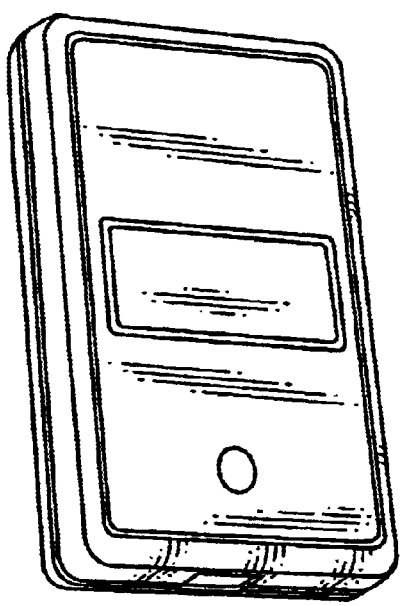
FIG. 6 depicts a monitor for measuring electrocurrent.

Characteristics of the monitor shown in FIG. 6 include: 1) Measurement of current at fixed potential; 2) LCD Screen; 3) Hand-held, battery powered monitor; 4) Push button to start measurement; 5) 5 seconds reading; and 6) Software/internet capability in development.

Disposable Base Sensor

Figure 7A:
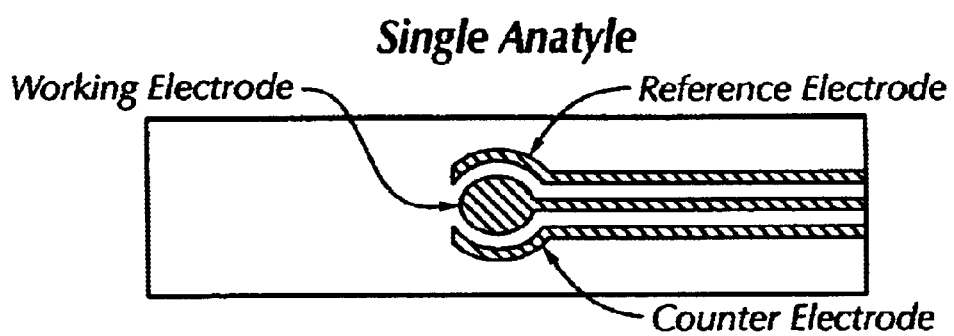
FIG. 7(A & B) depicts a disposable base sensor.
Figure 7B:
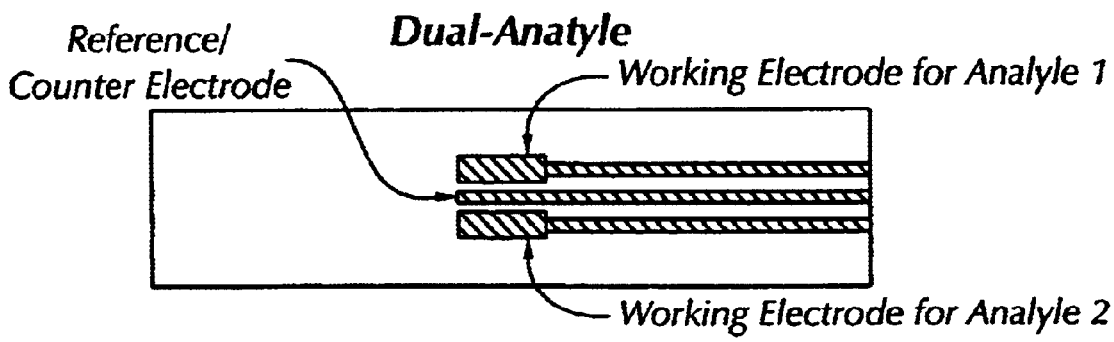

Characteristics of the disposable base sensor shown in FIG. 7 include: 1) Screen printing technique using carbon and Ag/AgCl inks; 2) Mass production at low cost; 3) Antibody immobilized on sensor surface; 4) Multiple sensor formats; and 5) Multi-analyte capability.

Disposable Sensor Assembly

Figure 8A:
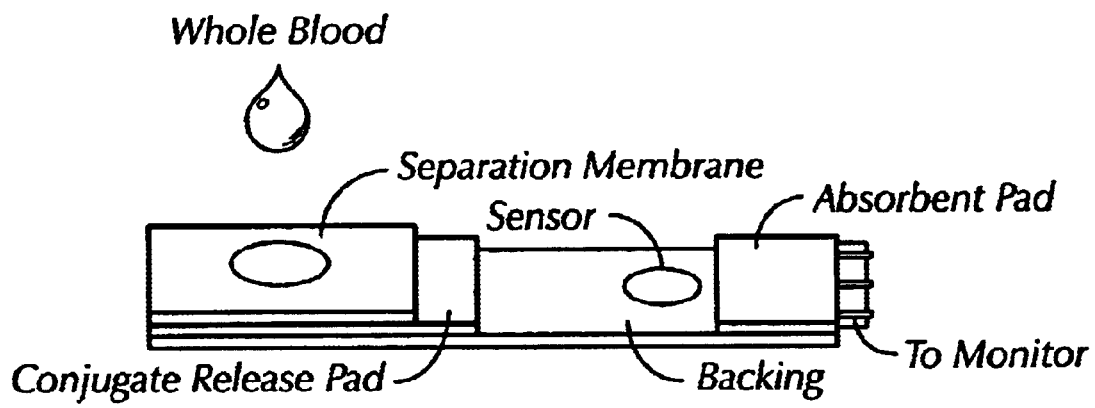
FIG. 8(A & B) depicts a disposable sensor assembly.
Figure 8B:
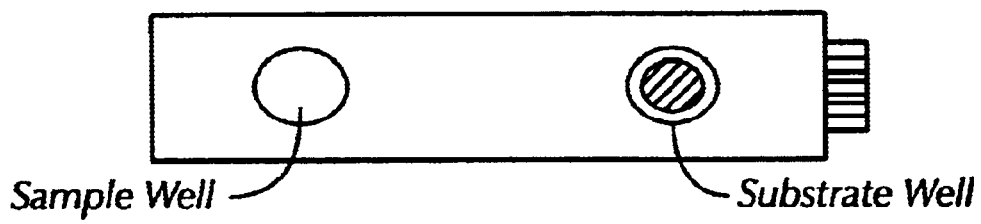
Figure 9:
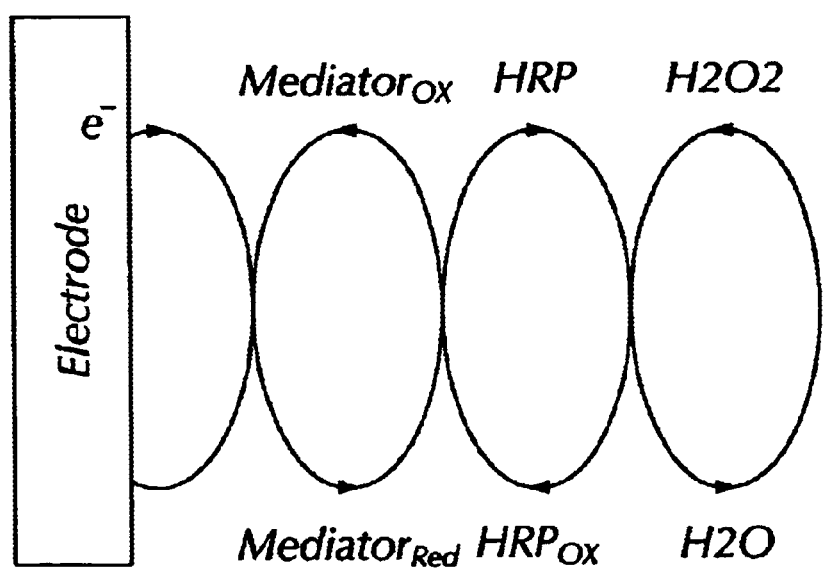
FIG. 9 depicts a detection scheme using HRP.

Characteristics of the disposable sensor assembly shown in FIG. 8 include: 1) Incorporation of base sensor, dry reagents, and other components; 2) Lateral flow of liquid; 3) Immuno-concentration effect; 4) Self-contained case; 5) Compatibility for a variety of sample matrixes.

Detection Scheme

Horseradish peroxidase (HRP) can be used in the system for the amplification of electrochemical signal. The activity of HRP is detected by a potentiostat using an electron pathway as shown below. HRP catalyzes the oxidation of TMB in the presence of hydrogen peroxide. TMB is then reduced at the electrode resulting in a current when the applied potential is at −200 mV. The magnitude of the current is directly proportional to the amount of HRP on the electrode surface.

Immobilization of Antibody

Antibody is immobilized on the working electrode of a sensor using our novel immobilization method. Antibody-based sensors were prepared by drop coating antibody solution, and followed by surface antibody stabilization. The finished sensor surface has high antigen binding capacity and long-term stability.

Sandwich Assay Format

Figure 10:
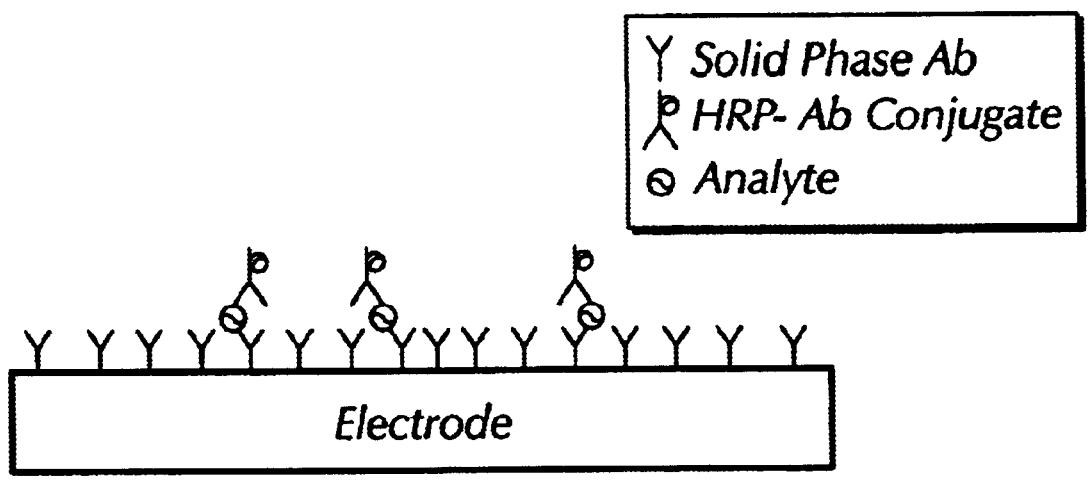
FIG. 10 illustrates a sandwich assay format.

The immunosensor assay is based on a sandwich principal where an analyte forms a "sandwich" between two antibodies (FIG. 10). One antibody is immobilized on the working electrode of the sensor and the other is conjugated to an enzyme. Each antibody binds to a different part of the analyte, enabling both to bind simultaneously.

The Lateral Flow Electroimmunosensor

The lateral flow electroimmunosensor is a disposable strip containing a base sensor immobilized with capture antibody, and incorporated with membranes and other reagents in dry form to carry out the analysis. One of the novel approaches in this design is to introduce a nylon mesh as a wicking agent to achieve a separation-free measurement. The sensor strip has a sample well and a detection well, and is designed for lateral flow of reagents and sample. The resulting sensor is a separation-free, disposable test strip that can be used for quantitative measurement of analytes in various sample matrixes.

Immunosensor for Troponin I Measurement

Cardiac Troponin I (cTnI) is the most specific marker for myocardial injury. The upper limit of normal range is 0.2 ng/ml. The Clinical significant range is 0.2–200 ng/ml. Experiments were conducted to optimize the assay conditions including the antibody loading on the sensor surface and the blocking of membrane to reduce non-specific signal.

Cardiac Troponin I (cTnI) assay procedure include the following steps: 1) Apply 50 $\mu$l of sample containing Troponin I to the sample well on the lateral flow immunosensor; 2) After 5 minutes, apply 50 $\mu$l of $H_2O_2$/TMB to the detection well on the sensor; and 3) Press the button on the monitor. Within 10 seconds, the monitor displays the measured current. Other assay conditions are:1) Immobilized mAb:70 ng/sensor; 2) 40 ng HRP-Ab/Conjugate pad; 3) 30 $\mu$m Nylon mesh (blocked with 10% sucrose, 5% BSA, 1% Triton/PBS); and 4) 50 $\mu$L buffer or serum sample.

Figure 11A:
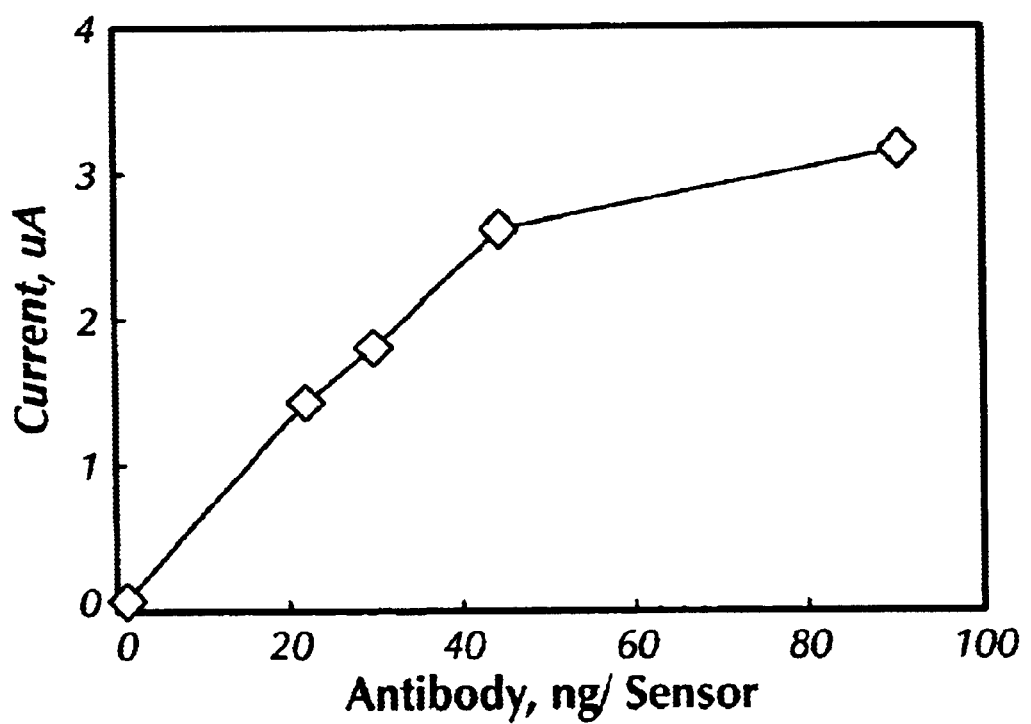
FIG. 11 shows troponin assay result. 11A shows effect of mAb loading on sensor surface; 11B shows effect of membrane blocking on non-specific signal; and 11C shows the assay result.
Figure 11B:
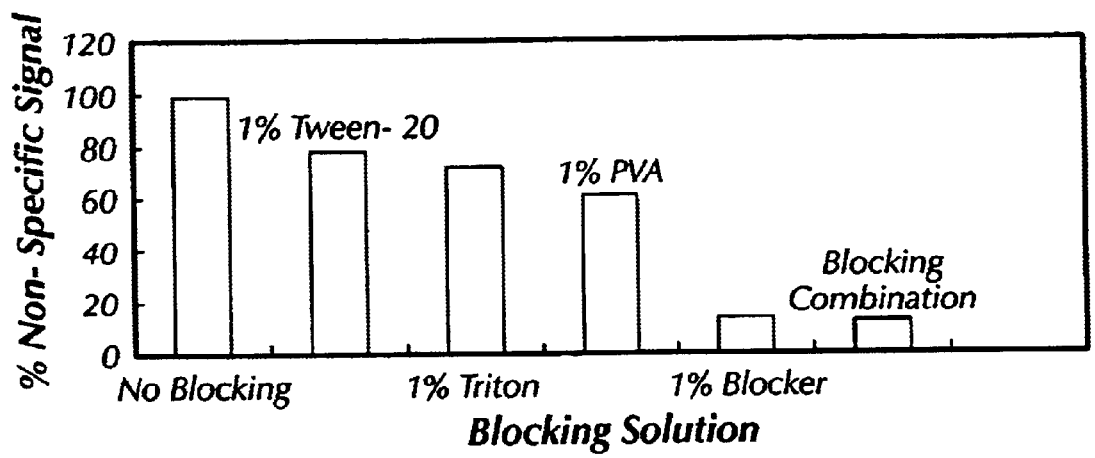
Figure 11C:
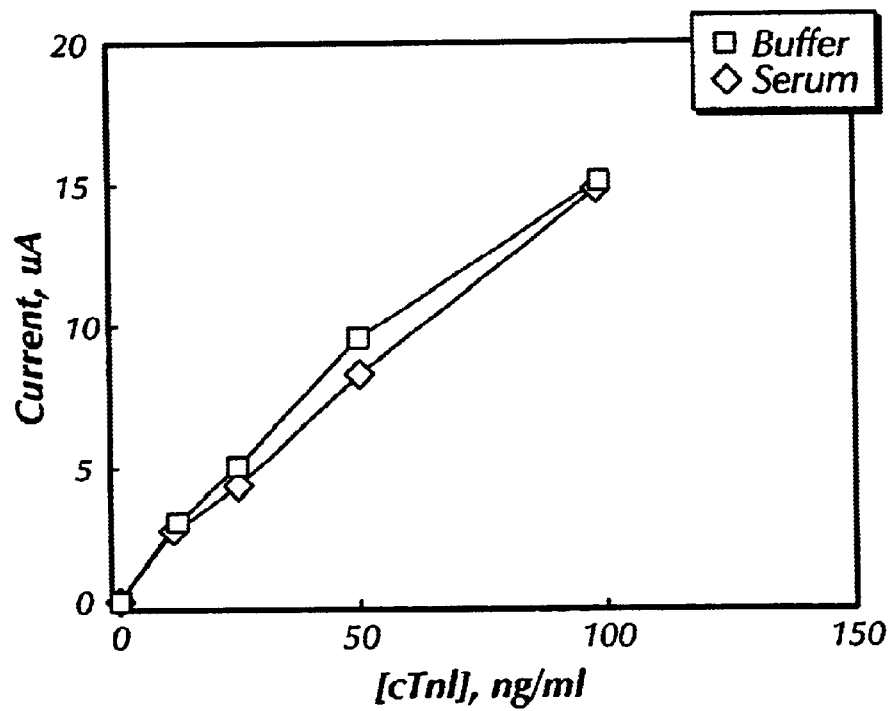
Figure 12:
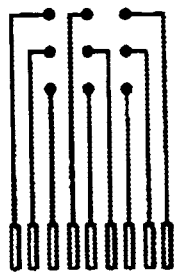
FIG. 12 shows several formats of sensor arrays that can be used for base sensor for multi-analyte detection.
Figure 12:
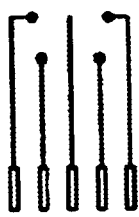
Figure 12:
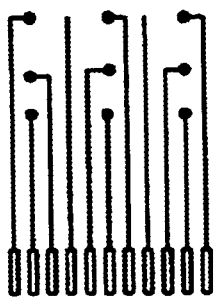
Figure 12:
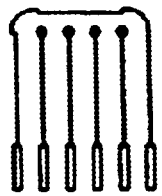
Figure 12:
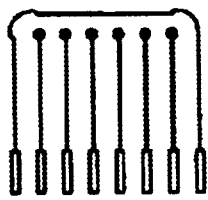

The assay results are shown in FIGS. 11A and B. Attributes of the system used in the above-described assay include: 1) User-friendly instrumentation; 2) Portable and low cost; 3) Sensitive, specific, and quantitative tests; 4) Rapid detection (assay time in minutes); 5) Simple assay procedure; and 6) Multi-analyte capability.

Conclusion

We have developed a new disposable immunosensor system. Feasibility of this system has been demonstrated for the quantitative measurement of human troponin I in serum sample. The system has the advantages of simplicity, high sensitivity, and low cost. Separation and lengthy incubation steps commonly necessary for immunoassays are eliminated due to the novel design of the immunosensor. The system characteristics allow the development of a new tool for clinical diagnosis of a wide range of analytes at the point-of-care settings.

While the invention has been described in detail with reference to certain preferred embodiments thereof, it will be understood that modifications and variations are within the spirit and scope of that which is described and claimed.

What is claimed is:

1. A device for detecting an analyte in a liquid sample, which device comprises:
   a) a solid support;
   b) an electrosensor immobilized on said solid support, said electrosensor comprises a working electrode and another electrode used as auxiliary and/or reference electrode;
   c) a capture reagent immobilized on said working electrode, said capture reagent binds to an analyte, if said analyte is present in a liquid sample; and
   d) conductive leads for connecting said electrodes to a readout device for electrochemical measurement,
   wherein the device further comprising a sample application area that is separate, but in fluid communication with the electrosensor via a wicking member having an open mesh structure that does not comprise an immobilized capture reagent, and wherein the wicking member having an open mesh structure provides for two dimensional transport of fluids from the application area to the electrosensor and faster flow rate, lower background noise and higher signal to noise ratio compared to a wicking member not having an open mesh structure.

2. The device of claim 1, wherein the solid support comprises a material selected from the group consisting of polyester, polyvinyl chloride (PVC), polyvinylidene fluoride (PVDF), paper, nylon, fiberglass, polyethylene, nitrocellulose, and a combination thereof.

3. The device of claim 1, wherein the electrosensor comprises a working electrode, an auxiliary electrode and a reference electrode.

4. The device of claim 3, wherein the working electrode and/or auxiliary electrode comprise(s) a screen-printed carbon conductor and the reference electrode comprises a screen-printed silver or silver/silver chloride conductor.

5. The device of claim 1, wherein the capture reagent is selected from the group consisting of a cell, a cellular organelle, an inorganic molecule, an organic molecule and a mixture thereof.

6. The device of claim 5, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

7. The device of claim 6, wherein the protein is an antibody, avidin/strepavidin, protein A or protein G.

8. The device of claim 1, wherein the capture reagent is immobilized on the working electrode in a buffered organic solution containing a ketone or an aliphatic alcohol.

9. The device of claim 8, wherein the aliphatic alcohol is isopropyl alcohol.

10. The device of claim 1, wherein the capture reagent specifically binds to the analyte.

11. The device of claim 1, wherein the analyte is selected from the group consisting of a cell, a cellular organelle, an inorganic molecule, an organic molecule and a mixture thereof.

12. The device of claim 1, wherein the analyte is alpha-fetoprotein, prostate-specific antigen, cardiac troponins, c-reactive protein (CRP), or human chorionic gonadotropin, or a marker for HBV, HAV, HCV or HIV infection.

13. The device of claim 1, further comprising an analyte bound to the capture reagent, said analyte contains a label that generates electrode current.

14. The device of claim 13, wherein the label is an enzyme.

15. The device of claim 14, wherein the enzyme is horseradish peroxidase and the device further comprises an enzymatic substrate that is hydrogen peroxide and an electron transfer mediator that is ferrocene, or a derivative thereof, benzoquinone, ascorbic acid or 3,3',5,5' tetramethylbenzidine.

16. The device of claim 1, further comprising a cover casing having a liquid sample application aperture and a detection aperture.

17. The device of claim 1, wherein the sample application area contains movably bound labeled analyte, said labeled analyte is dissolved or suspended into the sample liquid and carried to the capture reagent immobilized on the electrosensor by the sample fluid, and said label on said analyte generates electrocurrent.

18. The device of claim 1, wherein the sample application area contains movably bound labeled detection reagent, said labeled detection reagent is dissolved or suspended into the sample liquid, binds to the analyte, if there is any, carried to the capture reagent immobilized on the electrosensor by the sample fluid to form a sandwich comprising the immobilized capture reagent-analyte-labeled detection reagent, and said label on said detection reagent generates current.

19. The device of claim 18, wherein the movably bound labeled detection reagent specifically binds to the analyte, if there is any, in the sample fluid.

20. The device of claim 18, wherein the movably bound labeled detection reagent is an antibody.

21. The device of claim 18, wherein the label is an enzyme.

22. The device of claim 21, wherein the enzyme is horseradish peroxidase and the device further comprises an enzymatic substrate that is hydrogen peroxide and an electron transfer mediator that is ferrocene, or a derivative thereof, benzoquinone, ascorbic acid or 3,3',5,5' tetramethylbenzidine.

23. The device of claim 1, wherein the wicking member comprises a mesh having mesh opening in the range from about 0.45 $\mu$m to about 100 $\mu$m.

24. The device of claim 1, further comprising a filter in the application area, said filter removes insoluble or insuspendable material(s) from the sample fluid.

25. The device of claim 24, wherein the filter removes insoluble or insuspendable material(s) from a sample blood.

26. The device of claim 1, further comprising an absorptive sink in fluid communication with the electrosensor, said sink having sufficient porosity and capacity to absorb excess liquid or allow excess liquid to be washed out of the device.

27. The device of claim 26, wherein the absorptive sink is a pad of absorbent material.

28. The device of claim 1, which comprises an absorptive sink, an electrosensor and an application area that are linearly arranged in order.

29. The device of claim 1, further comprising an enzyme substrate and an electron transfer mediator localized on or in proximity to the electrosensor, said substrate and mediator is controllably released.

30. A device for detecting an analyte in a liquid sample, which device comprises:

a) a base sensor strip having a working electrode, a reference electrode, and an auxiliary electrode coated on a plastic substrate, whereon a capture reagent is immobilized on the working electrode, said sensor strip having conductive leads for attaching the electrodes to a readout device for electrochemical measurement;

b) a cover casing having a liquid sample application aperture and a detection aperture;

c) an application zone for receiving a fluid containing an analyte from the application aperture, said application zone, in dry unused form, containing a labeled detection reagent specifically binds to said analyte, if said analyte is present said fluid, wherein said labeled reagent is released into mobile form when in contact with the liquid sample;

d) a detection zone in fluid communication with the electrodes in the presence of a liquid sample received from the application aperture;

e) a wicking member having an open mesh structure that does not comprise an immobilized capture reagent and that carries the liquid sample from the application zone to the detection zone by capillary action, wherein the wicking member having an open mesh structure provides for two dimensional transport of fluids from the application area to the electrosensor and faster flow rate, lower background noise and higher signal to noise ratio compared to a wicking member not having an open mesh structure and wherein said analyte is sandwiched between the detection reagent and the capture reagent immobilized on the electrode surface; and f) an absorbent sink placed in partial contact with the wicking member at the end of the flow path to absorb any excess fluid from the detection zone.

31. A kit for detecting an analyte in a liquid sample, which kit comprises:

a) the device of claim 1; and b) an effective amount of an electron transfer mediator and a substrate.

32. A device for detecting an analyte in a liquid sample, which device comprises a sample application area that is in fluid communication with an electrosensor via a wicking member, wherein the wicking member has an open mesh structure that does not comprises an immobilized capture reagent that binds to an analyte, and wherein the wicking member having an open mesh structure provides for two dimensional transport of fluids from the application area to the electrosensor and faster flow rate, lower background noise and higher signal to noise ratio compared to a wicking member not having an open mesh structure.

33. The device of claim 32, wherein the wicking member comprises a nylon mesh having mesh opening in the range from about 0.45 $\mu$m to about 100 $\mu$m.

34. The device of claim 1, wherein the wicking member comprises a nylon net.

35. The device of claim 34, wherein the nylon net has a mesh opening from 11 $\mu$m to 100 $\mu$m.

36. The device of claim 34, wherein the nylon net has a mesh opening from 80 $\mu$m to 100 $\mu$m.

* * * * *